United States Patent
Rowland et al.

(10) Patent No.: US 10,889,795 B2
(45) Date of Patent: Jan. 12, 2021

(54) SYSTEM AND METHOD FOR COOLING PRETREATED BIOMASS

(71) Applicant: Iogen Energy Corporation, Ottawa (CA)

(72) Inventors: Stephen A. Rowland, Brownsburg-Chatham (CA); Chris Mallalieu, Ottawa (CA); Ryan Taylor, Nepean (CA); Ziyad Rahme, Ottawa (CA)

(73) Assignee: IOGEN ENERGY CORPORATION, Ottawa (CA)

( * ) Notice: Subject to any disclaimer, the term of this patent is extended or adjusted under 35 U.S.C. 154(b) by 302 days.

(21) Appl. No.: 15/779,001

(22) PCT Filed: Nov. 24, 2016

(86) PCT No.: PCT/CA2016/051382
§ 371 (c)(1),
(2) Date: May 24, 2018

(87) PCT Pub. No.: WO2017/088061
PCT Pub. Date: Jun. 1, 2017

(65) Prior Publication Data
US 2018/0355303 A1 Dec. 13, 2018

Related U.S. Application Data

(60) Provisional application No. 62/259,830, filed on Nov. 25, 2015.

(51) Int. Cl.
*C08H 8/00* (2010.01)
*C12M 1/00* (2006.01)
(Continued)

(52) U.S. Cl.
CPC .............. *C12M 45/20* (2013.01); *C08H 8/00* (2013.01); *C10L 1/02* (2013.01); *C12M 41/12* (2013.01);
(Continued)

(58) Field of Classification Search
None
See application file for complete search history.

(56) References Cited

U.S. PATENT DOCUMENTS

| 5,338,366 A | 8/1994 | Grace et al. |
| 5,789,210 A | 8/1998 | Ho et al. |

(Continued)

FOREIGN PATENT DOCUMENTS

| CA | 2918175 A1 | 2/2015 |
| EP | 0450430 B1 | 10/1991 |

(Continued)

OTHER PUBLICATIONS

International Search Report and Written Opinion issued in corresponding International Application No. PCT/CA2016/051382 dated Feb. 1, 2017 (10 pages).

*Primary Examiner* — Chester T Barry
(74) *Attorney, Agent, or Firm* — Venable LLP

(57) ABSTRACT

Discharging pretreated biomass from a pretreatment reactor and mixing the discharged pretreated biomass with a cooling liquid in a vessel provides a cooled slurry having a consistency that is less than about 12 wt %. Since the consistency is relatively low, the cooled slurry may be pumped to a higher elevation using standard pumping equipment. At the higher elevation, the cooled slurry may be separated into a first stream comprising a liquid component of the slurry and a second other stream comprising a solid component of the slurry (e.g., having a consistency between about 15 wt % and 40 about wt %). The solid component may be fed to an (Continued)

inlet of a hydrolysis reactor, while the liquid component may be fed to a cooling system that provides a cooled stream. The cooled stream may then be cycled back to the vessel.

20 Claims, 6 Drawing Sheets

(51) Int. Cl.
    *C10L 1/02*           (2006.01)
    *C13K 1/02*           (2006.01)
    *C12P 7/10*            (2006.01)
    *C12P 7/16*            (2006.01)
    *C12M 1/33*          (2006.01)
    *C12M 1/34*          (2006.01)

(52) U.S. Cl.
    CPC ............ *C12M 45/02* (2013.01); *C12M 45/04* (2013.01); *C12M 45/09* (2013.01); *C12P 7/10* (2013.01); *C12P 7/16* (2013.01); *C13K 1/02* (2013.01); *C12P 2201/00* (2013.01); *C12P 2203/00* (2013.01); *Y02E 50/10* (2013.01)

(56) References Cited

U.S. PATENT DOCUMENTS

| | | |
|---|---|---|
| 5,866,382 A | 2/1999 | Hallborn et al. |
| 6,475,768 B1 | 11/2002 | Otero et al. |
| 6,582,944 B1 | 6/2003 | Hallborn et al. |
| 7,527,927 B1 | 5/2009 | Ho et al. |
| 7,527,951 B2 | 5/2009 | Londesborough et al. |
| 7,566,383 B2 | 7/2009 | Everett et al. |
| 7,622,284 B2 | 11/2009 | Op Den Camp et al. |
| 8,017,820 B2 | 9/2011 | Foody et al. |
| 8,328,947 B2 | 12/2012 | Anand et al. |
| 8,709,770 B2 | 4/2014 | Harlick et al. |
| 8,871,061 B2 | 10/2014 | Beldring et al. |
| 9,528,135 B2* | 12/2016 | Romero .................. C12P 19/14 |
| 9,920,345 B2* | 3/2018 | Larsen ..................... C12P 7/10 |
| 10,087,578 B2* | 10/2018 | Dohrup ................... C10L 5/44 |
| 2009/0035826 A1 | 2/2009 | Tolan et al. |
| 2011/0008863 A1 | 1/2011 | Zhu et al. |
| 2012/0036768 A1 | 2/2012 | Phillips et al. |
| 2012/0052534 A1* | 3/2012 | Harlick .................. C12M 45/06 |
| | | 435/105 |
| 2012/0122162 A1 | 5/2012 | Romero et al. |
| 2012/0125549 A1 | 5/2012 | Romero et al. |
| 2012/0231510 A1* | 9/2012 | Rao ................ C12Y 302/01091 |
| | | 435/99 |
| 2012/0264071 A1 | 10/2012 | Kleijn |
| 2012/0289685 A1 | 11/2012 | Hallberg et al. |
| 2013/0071903 A1 | 3/2013 | Rowland et al. |
| 2014/0087432 A1 | 3/2014 | Nguyen et al. |
| 2014/0120594 A1 | 5/2014 | Foody et al. |
| 2015/0165709 A1 | 6/2015 | Miller et al. |
| 2015/0176034 A1 | 6/2015 | Ramos et al. |
| 2015/0240198 A1 | 8/2015 | Romero et al. |
| 2016/0215448 A1 | 7/2016 | Dohrup et al. |
| 2017/0362618 A1 | 12/2017 | Nguyen |

FOREIGN PATENT DOCUMENTS

| | | |
|---|---|---|
| WO | 2006/026863 A1 | 3/2006 |
| WO | 2008/041840 A1 | 4/2008 |
| WO | 2010/022511 A1 | 3/2010 |
| WO | 2015/012853 A1 | 1/2015 |
| WO | 2015/018423 A1 | 2/2015 |

* cited by examiner

SYSTEM AND METHOD FOR COOLING PRETREATED BIOMASS

The present application is a national-stage entry under 35 U.S.C. § 371 of International Patent Application No. PCT/CA2016/051382, published as WO 2017/088061 A1, filed Nov. 24, 2016, which claims priority to U.S. Provisional Application No. 62/259,830, filed Nov. 25, 2015, the entire disclosure of each of which is incorporated by reference herein.

TECHNICAL FIELD

The present disclosure relates to a system and method for hydrolyzing biomass, and in particular, to a system and method for cooling pretreated biomass prior to hydrolysis.

BACKGROUND

The production of transportation fuels (e.g., ethanol) from biomass continues to attract interest, due to the low cost and wide availability of biomass, and because biofuels may be used to displace the use of fossil fuels. For example, ethanol may be blended into gasoline at predetermined concentrations (e.g., 10%).

First generation biofuels, also referred to as conventional biofuels, are made from biomass that contains sugar, starch, or vegetable oil. For example, ethanol may be produced by fermenting sugars that are easily extracted from sugar crops (e.g., sugar cane or sugar beets), or may be produced by fermenting sugars derived from starch-based feedstocks (e.g., corn grain, barley, wheat, potatoes, cassava). In fact, the diversion of farmland or crops for first generation biofuel production has led to much debate about increased food prices and/or decreased food supplies associated therewith. In addition, there are concerns related to the energy and environmental impact of these production processes.

Second generation biofuels, also referred to as advanced biofuels, wherein the biomass contains lignocellulosic material and/or is obtained from agricultural residues or waste (e.g., corn cobs, corn stover (e.g., stocks and leaves), bagasse, wood chips, wood waste), may allay some of these concerns. For example, when bioethanol produced using second generation processes (i.e., also referred to as cellulosic ethanol) is derived from agricultural waste or residue, its production should not affect the food supply. In fact, tremendous effort is currently being expended to advance cellulosic ethanol production processes.

Lignocellulosic biomass typically contains cellulose, hemicellulose and lignin, each of which is present in plant cell walls. Cellulose (e.g., a type of glucan) is an unbranched chain polysaccharide including hexose (C6) sugar monomers (e.g., glucose). Hemicellulose is a branched chain polysaccharide that may include different pentose (C5) sugar monomers (e.g., xylose and arabinose) in addition to glucose. Lignin is a complex organic polymer, which typically includes cross-linked phenol polymers. Although generally insoluble in water at mild conditions, lignin may be soluble in varying degrees in dilute acid or base alkali. The ratio and/or structure of these components may vary depending on the source of the biomass.

The production of ethanol from lignocellulosic biomass most often involves breaking down the cellulose and/or hemicellulose into the constituent sugars, which may then be fermented. Unfortunately, the cellulose, hemicellulose, and/or lignin found in lignocellulosic biomass is typically structured within the plant walls to resist degradation. For example, lignin, which may be the most recalcitrant component of lignocellulosic biomass, is believed to be tightly bound to the cellulose and/or hemicellulose.

In general, lignocellulosic biomass may be broken down into sugars in one or more stages, wherein at least one stage includes a chemical hydrolysis (e.g., which may include the addition of acid, base, and/or heat) and/or an enzymatic hydrolysis (e.g., which includes using enzyme(s)).

For example, one common approach to converting lignocellulosic biomass to sugar(s) includes (a) a pretreatment stage, followed by (b) an acid or enzymatic hydrolysis. In this approach, the goal of the pretreatment stage may be to break down the lignin structure and/or disrupt the crystalline structure of the cellulose, so that the acids or enzymes used in the subsequent hydrolysis can easily access and hydrolyze the cellulose to sugar, which may then be fermented to ethanol.

In general, any pretreatment method that improves the rate and/or yield of sugar in the hydrolysis (e.g., by liberating the cellulose from the lignin and/or by making the cellulose more accessible) may be used. Some examples of pretreatments include dilute acid pretreatment, alkali pretreatment (e.g., lime), ammonia fiber expansion, autohydrolysis (e.g., hot water extraction that does not require the addition of acid or base), steam explosion, organic solvent, and/or wet oxidation. Alternatively, another pretreatment is used.

In many, but not all, cases, pretreatment will involve heating and/or adding heat to the lignocellulosic biomass in the presence of water (e.g., in a reactor under pressure). The presence of heat and water may disrupt the hydrogen bonds in the lignocellulosic feedstock and cause the biomass to swell. For example, the pretreatment may include injecting high pressure steam into a reactor containing the lignocellulosic biomass. In most of these cases the pretreatment temperature will be below about 300° C. For example, the pretreatment temperature may be between about 130° C. and about 240° C., or between about 180° C. and about 230° C., while the pressure may be between 28 psig and about 700 psig, or between about 145 psig and about 365 psig. The pretreatment reaction time may be between a few seconds up to 30 mins or longer.

Although the presence of water may be advantageous in terms of producing a disrupted and/or hydrated substrate, large amounts of water may increase the amount of heat required for the biomass to reach the desired pretreatment temperature. For example, if the lignocellulosic biomass is heated by injecting steam into the pretreatment reactor, more steam will be required for low consistency biomass than for high-consistency biomass (e.g., in order to achieve the same temperature within the reactor).

In general, the consistency refers the amount of undissolved dry solids or "UDS" of a sample, and is often expressed as a ratio on a weight basis (wt:wt), or as a percent on a weight basis, for example, % (w/w), also denoted herein as wt %. For example, consistency may be determined by filtering and washing the sample to remove dissolved solids and then drying the sample at a temperature and for a period of time that is sufficient to remove water from the sample, but does not result in thermal degradation of the sample. After water removal, or drying, the dry solids are weighed and the weight of water in the sample is the difference between the weight of the sample and the weight of the dry solids.

In general, water may be also added to lignocellulosic feedstock in order to form a slurry and thus facilitate the transportation and mechanical handling of the feedstock (e.g., pumping). For example, lignocellulosic feedstock slurry, which includes lignocellulosic feedstock pieces or particles in water, is most easily pumped when it has a consistency between about 1 and about 10 wt % undissolved dry solids.

In addition to facilitating pumping of the lignocellulosic biomass, using low consistency slurries may result in less damage to the equipment (e.g., due to erosion and/or corrosion). In contrast, using relatively high consistency slurries may be advantageous for pretreatment (e.g., as discussed in US Pat. Pub. No. 20130071903). For example, in pretreatments having a heating step, the amount of energy required for heating is related to the total mass of the feedstock slurry, including the water added for conveying the feedstock. Accordingly, using a relatively high consistency feedstock may reduce the energy required for heating in pretreatment (e.g., whether heat is provided by a heating jacket, the addition of hot water, and/or the addition of steam). In addition, using a relatively high consistency pretreatment system may also be advantageous in terms of reduction of capital cost (e.g., smaller downstream reactors) and/or operating costs (e.g., less energy for downstream heating, cooling and/or evaporating). Moreover, water usage costs may be reduced, which is especially advantageous in arid climates where water is at a premium.

One method for reducing water content, and the consequent energy requirements for heating during pretreatment, is to dewater the incoming feedstock slurry prior to carrying out pretreatment, as for example, described in WO 2010/022511. For example, dewatered feedstock may be produced by various devices, such as plug screw feeders and pressurized screw presses. In some instances, the water content of the feedstock is reduced so that the solids content is high enough for plug formation to occur. Dewatering can take place within a plug formation device or dewatering and plug formation can be carried out in separate pieces of equipment. Alternatively, it is possible to eliminate dewatering upstream of plug formation if the feedstock solids content is already at a desired high consistency.

However, despite the foregoing advantages associated with relatively high consistency slurries, their handling downstream of pretreatment can pose problems. For example, in order for conventional stirred reactors to mix the highly viscous slurry effectively (e.g., during enzymatic hydrolysis), a very large power input may be required. Moreover, specialized equipment may be required to convey the pretreated lignocellulosic biomass within the system. These requirements can significantly increase the capital and operating costs of the process. For example, although lignocellulosic biomass having a consistency below about 12 wt % may be transferred within the system with a conventional pump (e.g., a centrifugal pump), pumping pretreated lignocellulosic biomass having a consistency greater than about 12 wt % may require a medium consistency pump (e.g., a special centrifugal pump or a positive displacement pump), whereas pumping pretreated lignocellulosic biomass having a consistency greater than about 15 wt % may require a positive displacement pump. Unfortunately, the cost of these specialized pumps is significantly higher (e.g., compared to pumps used to pump pretreated biomass having a consistency less than about 12 wt %). In addition, positive displacement pumps, such as progressive cavity pumps, may have very high discharge pressures and/or have high wear rates. Furthermore, the diameter of the pipes used to transport these highly viscous slurries may need to be relatively large in order to reduce pressure drop (i.e., since high flow velocities and/or high fluid viscosities result in a larger pressure drop across a section of pipe and since low flow velocities mean larger pipes). For example, although lignocellulosic biomass having a consistency below about 12 wt % may be transported in a pipe with a velocity in the order of about 7 ft/sec, it may be better to pump lignocellulosic biomass having a consistency greater than about 15 % with a velocity lower than about 2 ft/sec to reduce pressure drop. Notably, pretreated lignocellulosic biomass, which often has a muddy texture, can be more challenging to pump than lignocellulosic biomass that has not been pretreated, even for the same consistencies. Alternatively, and/or additionally, lignocellulosic biomass having a consistency greater than about 15 wt % may be transferred within the system using horizontal conveyors (e.g., screw conveyors) and/or the force of gravity. More specifically, the outlet of one component may need to be vertically offset from the inlet of a successive component such that the transfer of the lignocellulosic biomass is gravity assisted. Unfortunately, if the number of components and/or size of the components is large, this may increase building height requirements.

Another challenge of pretreating high consistency slurries is that it can be very difficult to cool a thick slurry (e.g., having about 15% UDS or greater). For example, it may be desirable to cool the pretreated feedstock from the pretreatment temperature (e.g., which may be between 100° C. and 300° C., between 120° C. and 240° C., between 160° C. and 230° C., and/or between 180° C. and 230° C.) to a temperature that is compatible with microorganisms(s) used in a subsequent biological conversion. For example, enzymes used in hydrolysis may have optimum temperature ranges within the range between 20° C. and 90° C., between 30° C. and 65° C., between 40° C. and 60° C. between, or between 45° C. and 55° C. In general, the maximum and/or final pretreatment temperature may be dependent on the type of feedstock, whereas the temperature range of the hydrolysis may depend on the hydrolysis conditions (e.g., pH, amount and/or type of mixing, residence time) and/or the amount and/or type of enzyme(s) used (e.g., thermophilic and/or thermostable enzymes may tolerate higher temperatures).

One approach to cooling high consistency slurries (e.g., with at least 18 wt % UDS) is to discharge the hot pretreated slurry to one or more flash tanks. When the hot, high-pressure, slurry is discharged into a lower pressure tank, the slurry temperature drops, which releases heat that evaporates a portion of the slurry (i.e., to produce a flash stream). In general, the temperature of the cooled slurry is related to the pressure in the flash tank. If the flash tank is at atmospheric pressure, the high consistency slurry may be cooled from a relatively high temperature to about 100° C. However, if the flash tank is under vacuum, the high consistency slurry may be cooled from a relatively high temperature to below 100° C. (e.g., to 50° C.). Unfortunately, vacuum flash tanks are very expensive and large. Moreover, in order to facilitate transfer of the high consistency feedstock via gravity (e.g., to allow discharge from the vacuum flash tank via a dropleg and seal port), this voluminous component may need to be located at high elevation. In addition, transport of the cooled slurry may still require dilution, specialty pumps, and/or very large diameter pipes due to the high viscosity of the slurry. In addition, mixing pH adjusting chemicals and/or enzymes with a high consistency slurry may be difficult.

Another approach to cooling high consistency slurries is to add cold water to the slurry prior to transferring the slurry to the hydrolysis tank. Unfortunately, large volumes of cold water may be required in order to achieve the desired temperature. While adding large volumes of water may facilitate pumping with a low consistency pump, the excess water may increase the volume of liquid being fed to the hydrolysis reactor, which may necessitate the use of a larger vessel, and/or may result in a relatively dilute sugar solution (e.g., following hydrolysis) and/or ethanol solution (e.g., following fermentation). In fact, even if the cold water includes water recycled from another process (e.g., from stillage) challenges may still arise from the relatively dilute conditions.

In US Pat. Pub. No. 2015/0240198, Romero et al. discuss a system for cooling pretreated biomass prior to mixing with enzymes wherein a stream of partially hydrolyzed mixture is cooled and used as a coolant for the hot pretreated biomass. By recirculating the partially hydrolyzed mixture as a coolant, the amount of required cooling water is reduced. In addition there may not be a need to increase the size of the hydrolysis reactor, and the final sugar concentration yield may be increased. Unfortunately, the proposed system still relies on medium consistency pumps to transfer the pretreated slurry to the hydrolysis tank. In addition, since the recycled stream comprises a partially hydrolyzed mixture, which may be relatively viscous, the heat exchanger used to cool the slurry may not be as efficient as it would be for a less viscous slurry. Furthermore, since the cooled slurry may be transferred with a mixed consistency pump, the consistency of the slurry may not be high enough to be compatible with high consistency enzymatic hydrolysis processes.

SUMMARY

The present disclosure describes one or more embodiments wherein pretreated biomass is mixed with a cooling liquid to produce a cooled and less viscous slurry, thus facilitating pumping of the same. Prior to hydrolysis, the cooled slurry is subjected to a solid-liquid separation (e.g., via one or more decanter centrifuges), which removes at least a portion of the liquid to provide a liquid stream and a solids stream. The solids are conveyed to the hydrolysis and/or fermentation reactor, whereas the liquid stream (e.g., centrate) is cooled and recycled back into the process to provide at least a portion of the cooling liquid.

One aspect of the present disclosure is directed to a method for cooling pretreated biomass comprising: discharging pretreated biomass from a pretreatment reactor; mixing the discharged pretreated biomass with a cooling liquid in a vessel, the vessel including an outlet for providing a slurry; pumping the slurry to a solid-liquid separator, said solid-liquid separator for providing a first stream comprising a liquid component of the slurry and a second other stream comprising a solid component of the slurry; feeding at least a portion of the second other stream comprising the solid component to an inlet of a hydrolysis reactor; feeding at least a portion of the first stream comprising the liquid component to a cooling system to provide a cooled stream; and feeding at least a portion of the cooled stream to the vessel to provide cooling liquid.

Another aspect of the present disclosure is directed to a system for hydrolyzing biomass comprising: a pretreatment reactor for pretreating biomass prior to a hydrolysis reaction; a first cooling system in fluid communication with the pretreatment reactor for receiving pretreated biomass discharged from the pretreatment reactor, the first cooling system including a vessel having an inlet for receiving a cooling liquid, an agitator for mixing the pretreated biomass discharged from the pretreatment reactor with the cooling liquid, and an outlet for providing a slurry comprising pretreated biomass; a solid-liquid separating system for separating the slurry into a first stream comprising a liquid component of the slurry and a second other stream comprising a solid component of the slurry; a hydrolysis reactor in fluid communication with the solid-liquid separating system, the hydrolysis reactor having an inlet for receiving at least a portion of the second other stream comprising the solid component; a second cooling system for reducing the temperature of at least a first portion of the first stream comprising the liquid component to provide a cooled stream; at least one pipe for conveying at least a portion of the cooled stream to the vessel to provide cooling liquid; and a pump for transferring the slurry from the vessel to the solid-liquid separating system.

Yet another aspect of the present disclosure is directed to a method for hydrolyzing biomass comprising: discharging biomass from a pressurized pretreatment reactor into a flash tank, a difference in pressure between the pressurized pretreatment reactor and the flash tank causing the biomass to cool from a first temperature to a second temperature; mixing the discharged biomass with a cooling liquid in a mixing zone of the flash tank to form a slurry having a consistency that is less than about 12 wt %, the slurry at a third temperature, the third temperature lower than the second temperature; pumping the slurry having a consistency that is less than about 12 wt % up to a solid-liquid separator, said solid-liquid separator for providing a first stream comprising a liquid component of the slurry and a second other stream comprising a solid component of the slurry, said second other stream having a consistency between about 15 wt % and about 40 wt %; feeding at least a portion of the second other stream comprising the solid component to an inlet of a hydrolysis reactor; feeding at least a portion of the first stream comprising the liquid component to a cooling system to provide a cooled stream, the cooled stream having a fourth temperature, the fourth temperature lower than the third temperature and less than about 50° C.; and feeding at least a portion of the cooled stream to the flash tank.

Yet another aspect of the present disclosure is directed to a system for hydrolyzing biomass comprising: a pretreatment reactor for pretreating biomass; a hydrolysis reactor for hydrolyzing pretreated biomass; and a substantially closed-loop cooling system disposed downstream of the pretreatment reactor and upstream of the hydrolysis reactor for cooling pretreated biomass prior to hydrolysis, said substantially closed-loop cooling system comprising: a vessel having an inlet for receiving a cooling liquid, a mixing zone for mixing biomass discharged from the pretreatment reactor with the cooling liquid, and an outlet for providing a slurry comprising pretreated biomass; a solid-liquid separator for removing liquid from the slurry such that biomass having a consistency greater than about 15 wt % is fed to the hydrolysis reactor; a cooling device for reducing the temperature of at least a portion of the liquid removed from the slurry to provide a cooled stream; and one or more conduits for conveying at least a portion of the cooled stream to the vessel.

DETAILED DESCRIPTION

Figure 1:
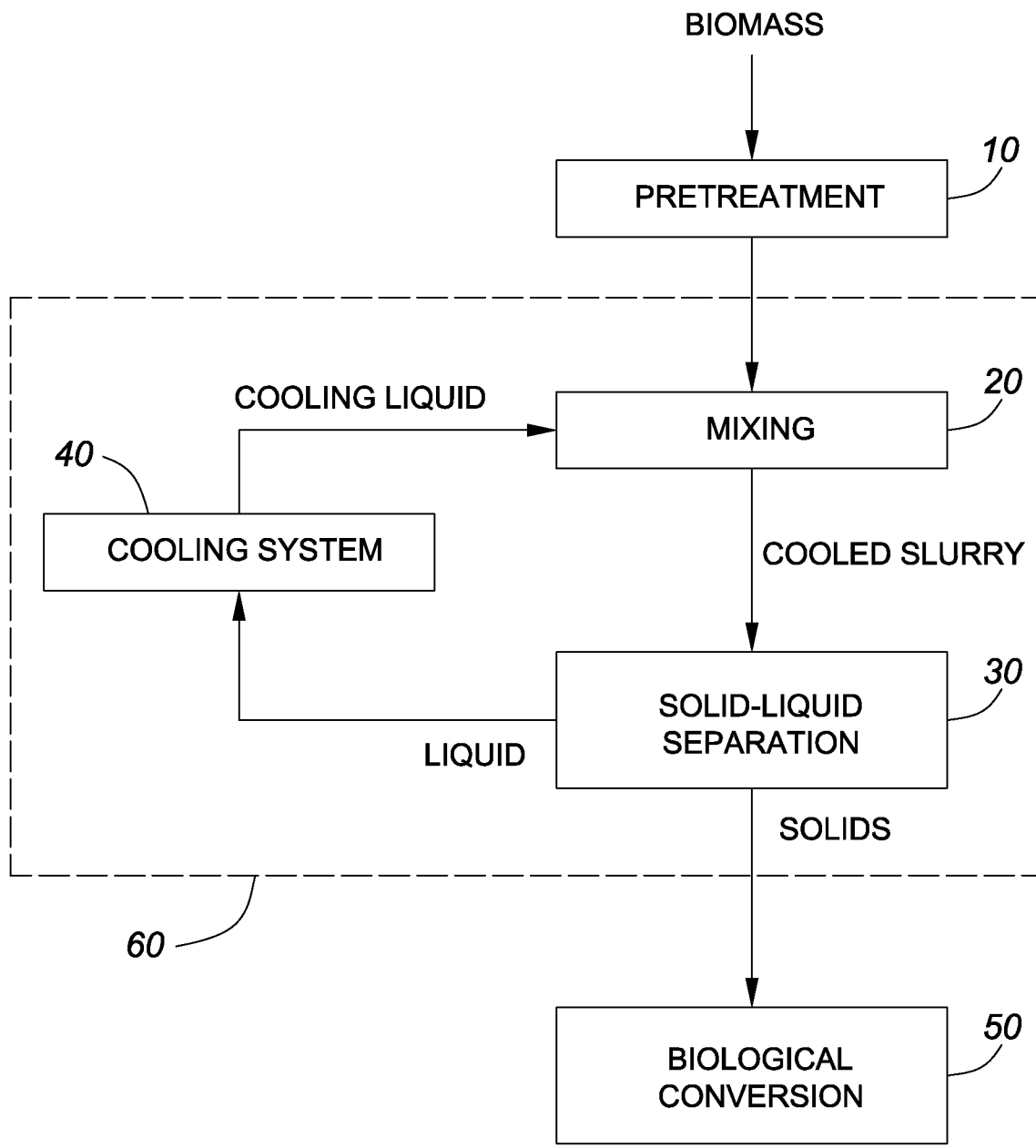
FIG. 1 is a flow diagram of a method according to one embodiment of the invention.

Certain exemplary embodiments of the invention now will be described in more detail, with reference to the drawings, in which like features are identified by like reference numerals. The invention may, however, be embodied in many different forms and should not be construed as limited to the embodiments set forth herein.

The terminology used herein is for the purpose of describing certain embodiments only and is not intended to be limiting of the invention. For example, as used herein, the singular forms "a," "an," and "the" may include plural references unless the context clearly dictates otherwise. The terms "comprises", "comprising", "including", and/or "includes", as used herein, are intended to mean "including but not limited to." The term "and/or", as used herein, is intended to refer to either or both of the elements so conjoined. The phrase "at least one" in reference to a list of one or more elements, is intended to refer to at least one element selected from any one or more of the elements in the list of elements, but not necessarily including at least one of each and every element specifically listed within the list of elements. Thus, as a non-limiting example, the phrase "at least one of A and B" may refer to at least one A with no B present, at least one B with no A present, or at least one A and at least one B in combination. The terms "first", "second", etc., may be used to distinguish one element from another, and these elements should not be limited by these terms. Unless defined otherwise, all technical and scientific terms used herein have the same meanings as commonly understood by one of ordinary skill in the art.

Referring to FIG. 1, there is shown a method in accordance with one embodiment of the invention. Biomass is fed to a pretreatment 10, which involves a heating step, to produce pretreated biomass. The pretreated biomass is cooled in a mixing stage 20, wherein a cooling liquid is mixed with the pretreated biomass. Once sufficient cooling liquid has been added to cool the biomass to a predetermined temperature and/or within a predetermined temperature range, the biomass is subjected to a solid-liquid separation 30, which removes at least a portion of the cooling liquid added in the mixing stage 20. A liquid stream produced by the solid-liquid separation 30 is recycled back to the mixing stage 20 after being cooled 40 (i.e., to provide at least a portion of the cooling liquid added in the mixing stage 20), thus providing a cooling loop 60. A solid stream produced by the solid-liquid separation 30 is fed to the biological conversion 50 (e.g., hydrolysis and/or fermentation).

Advantageously, the amount and/or temperature of the cooling liquid added in the mixing stage 20 may be selected such that the consistency of the pretreated biomass after mixing 20 is reduced to a point that it may be pumped to a subsequent stage using a relatively inexpensive pump (e.g., a centrifugal pump) and relatively small diameter piping (e.g., sized to provide a flow velocity between about 4 and 10 ft/sec). For example, in one embodiment the consistency is reduced to less than about 12 wt %. In one embodiment the consistency is reduced to less than about 10 wt %. In another embodiment, the consistency is reduced to about 8 wt %. This is particularly beneficial when the plant is designed such that that pretreated biomass needs to be transported to a relatively high elevation prior to the subsequent stage. For example, in some systems, the inlet to the hydrolysis reactor may be at a relatively high point in the system. Notably, since the solid-liquid separation reduces the consistency of the biomass, the amount of liquid added during cooling 20 should not affect downstream operations.

In fact, in one embodiment, the method illustrated in FIG. 1 provides a substantially closed-loop cooling system between pretreatment and the biological conversion (e.g., cooling loop 60 is a substantially closed-loop cooling system). More specifically, it provides a system wherein the cooling liquid used to reduce the temperature of the pretreated biomass is recycled directly without substantially affecting downstream reactions and/or vessels. The phrase "substantially closed-loop" refers to the fact that the degree of solid-liquid separation provided in the solid-liquid separation 30 may be selected to provide a predetermined consistency at the subsequent biological conversion and/or to account for the fact that additional liquids (e.g., pH adjusting chemicals, enzyme solutions, surfactant, water, etc.) may be added between pretreatment and the biological conversion. In embodiments where the desired consistency of the biomass at biological conversion is substantially the same as the consistency of the biomass discharged from pretreatment, the amount of liquid removed in the solid-liquid separation may be substantially equal to the amount of cooling liquid fed into the mixing stage (e.g., volume/unit time), or may be more than the amount of cooling liquid fed into the mixing stage if a substantial amount of other liquid has been added. Notably, this is particularly advantageous when biomass having a relatively high consistency is to be fed into the biological conversion (e.g., high relative to conventional hydrolysis reactions where the biomass initially fed to hydrolysis has a consistency that is less than 15 wt %). In embodiments wherein the amount of liquid removed in the solid-liquid separation is more than the amount of cooling liquid fed into the mixing stage, the excess liquid (e.g., which may be high in C5 sugars) may be carried forward in the process (e.g., to one or more fermentation reactors and/or to one or more hydrolysis reactors). In other embodiments (e.g., where the desired consistency of the biomass at hydrolysis is less than the consistency of the biomass discharged from pretreatment, or wherein some liquid is lost), the amount of liquid removed in the solid-liquid separation may be less the amount of cooling liquid fed into the mixing stage. In this latter embodiment, the cooling liquid may be topped up to the appropriate volume (e.g., using fresh water, recycled liquids, solutions of pH adjusting chemicals, etc.).

Advantageously, the cooling loop 60 also provides a point in the process wherein additional water, solutions (e.g., pH adjusting chemicals), and/or enzymes may be added to the biomass. For example, if the pretreatment involves heating the biomass at low pH conditions, then the pH may need to be adjusted prior to a subsequent enzymatic hydrolysis and/or fermentation. In one embodiment, a pH adjusting chemical (e.g., a neutralizing chemical) is introduced to the cooling water prior to mixing the biomass with the cooling water. Since the mixing 20 results in a slurry having a consistency that is less than about 12%, uniform distribution of the added chemical is achieved. In other embodiments, the pH adjusting chemical, enzymes, and/or other chemicals are added directly into the mixer and/or are introduced into the slurry at some point prior to the solid-liquid separation.

Biomass

Biomass refers to biological material derived from living, or recently living organisms. For example, biomass includes plant matter grown for use as biofuel, plant or animal matter used for the production of fibers, chemicals, or heat, and/or biodegradable wastes. In addition, the term biomass includes processed biomass (e.g., feedstock that has been subjected to one or more processing steps).

The biomass fed to the pretreatment 10 may include any biomass that is to be pretreated in at least one step that uses elevated temperatures, and thus needs to be cooled for a subsequent biological conversion (e.g., hydrolysis and/or fermentation).

In one embodiment, the biomass fed to the pretreatment 10 includes lignocellulosic feedstock or is derived from lignocellulosic feedstock.

By the term "lignocellulosic feedstock", it is meant any type of feedstock containing at least cellulose and lignin (e.g. may contain non-woody plan biomass and/or feedstock derived from plant biomass). For example, in one embodiment the combined content of cellulose, hemicellulose and lignin in lignocellulosic feedstock is greater than 25 wt % (w/w). In one embodiment, sucrose, fructose and/or starch are also present, but in lesser amounts than cellulose and hemicellulose.

Some examples of lignocellulosic feedstock and/or lignocellulosic derived feedstock include: (i) energy crops; (ii) residues, byproducts or waste from the processing of plant biomass in a facility or feedstock derived therefrom; (iii) agricultural residues; (iv) forestry biomass; (v) waste material derived from pulp and paper products; (vi) pulp and paper waste; and/or (vii) municipal waste including components removed from municipal waste.

Energy crops include biomass crops such as grasses, including C4 grasses, such as switch grass, energy cane, sorghum, cord grass, rye grass, miscanthus, reed canary grass, C3 grasses such as Arundo donax, or a combination thereof.

Residues, byproducts or waste from the processing of plant biomass in a facility of feedstock derived therefrom include residues remaining after obtaining sugar from plant biomass such as sugar cane bagasse, sugar cane tops and leaves, beet pulp, or residues remaining after removing sugar from Jerusalem artichoke or residues remaining after grain processing, such as corn fiber, corn stover or bran from grains.

Agricultural residues include, but are not limited to soybean stover, corn stover, sorghum stover, sugar cane tops and/or leaves, rice hulls, rice straw, barley straw, corn cobs, wheat straw, canola straw, oat straw, rye straw, oat hulls, corn fiber, and corn cobs. As used herein, straw refers to the stem, stalk and/or foliage portion of crops remaining after the removal of starch and/or sugar containing components for consumption, whereas stover includes the stalk and foliage portion of crops after the removal of starch and/or sugar containing components of plant material for consumption.

Forestry biomass includes recycled wood pulp fiber, sawdust, hardwood, softwood, trimmings and/or slash from logging operations. Pulp and paper waste includes waste from chemical pulping such as black liquor, spent sulfite liquor, sludge and/or fines.

Municipal waste includes post-consumer material or waste from a variety of sources such as domestic, commercial, institutional and/or industrial sources. For example, the term includes refuse from waste collection and/or sewage sludge.

In one embodiment, the biomass includes fresh lignocellulosic feedstock, partially dried lignocellulosic feedstock, fully dried lignocellulosic feedstock, or a combination thereof In one embodiment, the lignocellulosic feedstock is treated with a chemical and stored for a prolonged length of time. In one embodiment, the lignocellulosic feedstock is produced by plant breeding or by genetic engineering. In one embodiment, the biomass includes a mixture of fibers that originate from different kinds of plant materials, including mixtures of cellulosic and non-cellulosic feedstocks.

Biomass Preparation

In one embodiment, the biomass is treated in one or more preparatory steps prior to pretreatment 10 and/or as part of the pretreatment 10. Some examples of biomass preparation include size reduction, washing, slurry formation, soaking, dewatering, plug formation, addition of heat, and addition of chemicals (e.g., pretreatment and/or other). In general, these preparatory treatments may depend on the type of biomass and/or selected pretreatment.

In one embodiment, the biomass is subject to a size reduction. For example, in one embodiment, lignocellulosic feedstock having an average particle size greater than about 6 inches is subjected to size reduction. Some examples of suitable size reduction methods include, but are not limited to, milling, grinding, agitation, shredding, compression/expansion, and/or other types of mechanical action. Size reduction by mechanical action may be performed by any type of equipment adapted for the purpose, for example, but not limited to, hammer mills, tub-grinders, roll presses, refiners and hydrapulpers. In one embodiment, at least 90% by volume of the particles produced from the size reduction may have a length between about $\frac{1}{16}$ and about 6 inches. In one embodiment, the equipment for the particle size reduction is a hammer mill, a refiner or a roll press as disclosed in WO 2006/026863. In one embodiment, wherein the particle size of the feedstock is already between $\frac{1}{2}$ to 8 inches, the biomass is not subjected to size reduction.

In one embodiment, the biomass is washed to remove sand, grit, and/or other foreign particles that otherwise may cause damage to the downstream equipment. In one embodiment, the biomass is washed before, during, or subsequent to size reduction. In one embodiment, the biomass is not washed.

In one embodiment, the biomass is slurried in liquid (e.g., water), which allows the biomass to be pumped. In one embodiment, the biomass is slurried subsequent to size reduction. The desired weight ratio of water to dry biomass solids in the slurry may be determined by factors such as pumpability, pipe-line requirements, and other practical considerations. For example, in one embodiment, the biomass is slurried to provide a consistency between about 1 wt % and about 40 wt %, or 1 wt % and 20 wt %, or between about 4 wt % and about 10 wt %.

In one embodiment, the biomass is soaked in water and/or an aqueous solution (e.g., comprising a pretreatment chemical). In one embodiment, the biomass is soaked subsequent to being slurried (e.g., the slurried biomass is fed to a soaking tank). Feeding the slurried biomass to a soaking tank may allow pretreatment chemical(s) to more uniformly impregnate the biomass, which in turn may provide even cooking in the heating step of pretreatment. For example, soaking the feedstock in a solution comprising a pretreatment chemical (e.g., such as sulfuric acid, sulfurous acid, or an alkali) typically provides uniform impregnation of the biomass with the pretreatment chemical. Soaking the feedstock in water, may allow gaseous pretreatment chemicals (e.g., comprising sulfur dioxide) to more uniformly and/or completely impregnate the biomass during subsequent chemical addition steps. In general, uniform impregnation may ensure that some material is not overcooked and/or degraded due to high localized concentration of the pretreatment chemical, and/or that some material is not undercooked (e.g., which may result in low xylose yield and incomplete cellulose hydrolysis). Undercooking or overcooking of lignocellulosic feedstock may be particularly problematic when the heating step of pretreatment is conducted under medium or high solids consistency since the non-uniformity in the concentration of the pretreatment chemical and the temperature are more pronounced.

In one embodiment, soaking is conducted at low consistency. For example, in one embodiment, the soaking is conducted at a consistency between 1 and 20 wt % (wt:wt), between 2 and 18 wt %, or between 3 and 15 wt %. The soaking may be carried out at any suitable temperature and duration. For example, in one embodiment, soaking is carried out at 20° C. to 80° C. for a duration in the range between about 1 and 20 minutes. Soaking may be carried out in one or more batch or continuous vessels, or a combination thereof. The vessels may be mixed vessels, unmixed vessels, or a combination thereof.

In one embodiment, the biomass is dewatered to provide a desired consistency for the heating step of pretreatment. In one embodiment, the dewatering is achieved subsequent to the biomass being washed, slurried, and/or soaked. In one embodiment, the dewatering includes removing water from the biomass under pressure or at atmospheric pressure. In one embodiment, dewatering of the biomass is not provided. In one embodiment, wherein the biomass is subjected to dewatering after the soaking step, the water from dewatering is recycled back to the soaking step. In another embodiment, wherein the biomass is subjected to dewatering after the soaking step, the water from dewatering is not recycled back to the soaking step (e.g., such that the soaking step is part of a leaching stage and/or such that the liquid from the dewatering may be processed separately). In one embodiment, wherein the biomass is subject to dewatering after being slurried and/or after soaking in water, the water expressed from the biomass in dewatering is recycled back to the slurrying and/or soaking steps.

In one embodiment, dewatering is achieved using a drainer, filtration device, screen, screw press, extruder, or a combination thereof In one embodiment, dewatering is achieved using a centrifuge. In one embodiment, the dewatering is achieved prior to and/or as part of plug formation. Without being limiting, a plug formation device incorporating a dewatering section may be a pressurized screw press or a plug screw feeder, as described in WO 2010/022511, which is incorporated herein by reference. In one embodiment, wherein the biomass is subjected to dewatering under pressure, the pressure increase may be caused by one or more high pressure pumps. The pump, or other feeding device, may increase the pressure of the biomass prior to dewatering (e.g., from about 50 psig to about 900 psig, or about 70 psig to about 800 psig or about 140 psig to about 700 psig). The pressure may be measured with a pressure sensor located at a biomass inlet port on a dewatering device or a plug formation device that also dewaters the feedstock. Alternatively, the feedstock subjected to dewatering may be at atmospheric pressure, or at a pressure below about 50 psig.

In one embodiment, the biomass (e.g., which may or may not have been subject to a previous dewatering) is subject to plug formation. In general, plug formation may be considered an integration of lignocellulosic biomass particles into a compacted mass referred to herein as a plug. Plug formation devices may form a plug that acts as a seal between areas of different pressure. For example, plug formation devices may be used at the front end of a pressurized pretreatment reactor. In one embodiment, the biomass is fed to a plug formation device that dewaters the biomass and/or is disposed downstream of a dewatering device. In one embodiment, the plug formation device that dewaters the biomass includes a housing or shell with openings through which water can pass. Some examples of plug formation devices that dewater biomass include a plug screw feeder, a pressurized screw press, a co-axial piston screw feeder, and a modular screw device.

In one embodiment, the dewatered biomass may have a weight ratio of water to undissolved dry solids between about 0.5:1 (67 wt %) and about 5:1 (17 wt %), or between about 1:1 (50 wt %) and about 4:1 (20 wt %), or between about 1.5:1 (40 wt %) to about 4:1 (20 wt %), or between about 1.5:1 (40 wt %) and about 3.5:1 (22 wt %).

In one embodiment, the biomass is subject to a step that adds heat (e.g., applying extraneous heat, a hot liquid, and/or steam). In one embodiment, the biomass is heated as part of the soaking step, as part of a leaching step, or as a separate step. In one embodiment, the biomass is subjected to a steam addition step upstream of entering the pretreatment reactor. In another embodiment, the dewatered biomass is preheated prior to being fed to the pretreatment reactor. For example, in one embodiment, the dewatered biomass is fed to a downstream "heating chamber" or "high shear heating chamber" prior to being fed to a pretreatment reactor. For example, the heating chamber, which may be a horizontally-oriented or essentially horizontally-oriented elongate chamber, may include disintegrating elements for disintegrated the plug of biomass into particles and/or may include inlets for direct steam injection (e.g., to preheat the biomass and provide efficient heat transfer) and/or adding pretreatment chemicals. For example, in one embodiment, a pretreatment chemical such as sulfur dioxide may also be added during direct steam injection. In one embodiment, the biomass is preheated prior to being fed to the pretreatment reactor using a heating chamber as disclosed, for example, in US. Pat. No. 2013/0071903, which is hereby incorporated by reference. In one embodiment, the operating pressure and temperature of the heating chamber corresponds to the pressure and temperature of the downstream pretreatment reactor. In one embodiment, the biomass is resident in the heating chamber for a duration between about 1 seconds and about 120 seconds, or longer.

Pretreatment

In general, pretreatment refers to one or more steps wherein the biomass is treated such that the fiber structure thereof is disrupted and/or such that the cellulose in the biomass is more susceptible and/or accessible to enzymes in a subsequent hydrolysis.

In one embodiment, the pretreatment 10 includes feeding the biomass into a pretreatment reactor and heating the biomass therein (e.g., directly or indirectly) under pressure. Accordingly, the pretreatment reactor may include one or more valves for maintaining the pretreatment reactor a predetermined pressure (e.g., greater than about 90 psia and less than about 680 psia) and/or heating means for heating the biomass (e.g., a heating jacket and/or inlets for direct steam injection). Notably, direct steam injection may be advantageous in terms of quickly and uniformly heating high consistency biomass and/or for breaking down the biomass structure via steam explosion.

in one embodiment, the pretreatment 10 includes heating the biomass to a predetermined temperature or temperature range. In general, the predetermined temperature will be greater than about 100° C. For example, in one embodiment, the pretreatment temperature is between about 100° C. and about 300° C., between about 160° C. and about 280° C., and/or between about 180° C. and about 240° C. In one embodiment, the pretreatment temperature is about 190° C. In practice, there may be a time delay between the time at which the heating process is started and the time when the biomass reaches the predetermined pretreatment temperature.

In one embodiment, the pretreatment 10 includes heating the biomass in the pretreatment reactor under acidic or basic conditions. In one embodiment, the acidic or basic conditions are achieved by adding one or more pretreatment chemicals to the biomass. The pretreatment chemical(s) may be added to the biomass during a soaking step, prior to dewatering, prior to plug formation, into the heating chamber, into the plug formation device, into the pretreatment reactor, or any combination thereof. The pH may be measured by taking a sample of the biomass after the addition of pretreatment chemical(s) is complete, and measuring the pH at ambient temperature.

In one embodiment, the pretreatment chemical comprises one or more acids such that the biomass in the pretreatment reactor has a pH between about 0 and about 3.5, between about 0.5 and about 3, or between about 1.0 and about 2.5. In one embodiment, the one or more acids comprise sulfuric acid, sulfurous acid, hydrogen chloride, phosphoric acid, sulfur dioxide, oxalic acid, or a combination thereof.

In another embodiment, the pretreatment chemical comprises alkali and/or one or more bases such that the biomass in the pretreatment reactor has a pH between about 11 and about 13. In one embodiment, the alkali and/or one or more bases comprises sodium hydroxide, potassium hydroxide, ammonia, ammonium hydroxide, calcium carbonate, lime, or a combination thereof.

In another embodiment, the pretreatment chemical includes one or more oxidants such as oxygen and/or ozone.

The time that the biomass is held at the pretreatment temperature may be dependent on the type of feedstock, the pretreatment chemicals (e.g., if any), and/or the desired degree of pretreatment. In one embodiment, the degree of pretreatment is selected to convert most of the hemicellulose component to soluble sugars (e.g., xylose, mannose, arabinose, and glucose), but little of the cellulose component (e.g., which may be hydrolyzed in a subsequent enzymatic hydrolysis). For example, in one embodiment, the degree of pretreatment is selected such that the amount of xylan hydrolyzed to xylose is greater than about 50, about 60, about 70, about 80, or about 90 wt %. In another embodiment, the degree of pretreatment is selected such that substantially no xylan is hydrolyzed to xylose. In one embodiment, the degree of pretreatment is selected to minimize sugar degradation products such as furfural and 5-hydrolxymethyl furfural (HFM), which may inhibit enzymatic hydrolysis. In one embodiment, the degree of pretreatment is selected to maximize the amount of cellulose hydrolyzed to glucose.

In one embodiment, the pretreatment 10 is a dilute acid pretreatment selected to hydrolyze at least a portion of the hemicellulose component, but to minimize the hydrolysis of the cellulose component. In this embodiment, the pretreatment chemical is an acid such as sulfuric acid, hydrochloric acid, or oxalic acid, the pretreatment temperature is between about 120 and about 210° C., and the residence time in the pretreatment reactor is between seconds and hours (e.g., between about 10 seconds and about 120 minutes). For example, in one embodiment, the biomass is soaked in a 0.2-2.5% w/w solution of sulfuric acid prior to dewatering and steam injection.

In one embodiment, the pretreatment 10 is an $SO_2$ pretreatment selected to hydrolyze at least a portion of the hemicellulose component and to minimize the hydrolysis of the cellulose component. In this embodiment, the pretreatment chemical is sulfur dioxide and/or sulfurous acid, the pretreatment temperature is between about 180 and about 230° C., and the residence time in the pretreatment reactor is between seconds and minutes (e.g., between about 10 seconds and about 30 minutes, and more commonly less than about 10 minutes). In one embodiment, the biomass is soaked in water prior to dewatering, sulfur dioxide impregnation, and steam injection.

In one embodiment, the pretreatment 10 is an autohydrolysis, wherein acidic compounds released during the heating step (e.g., steam injection) accelerate the hemicellulose hydrolysis. In this embodiment, no pretreatment chemical is added, the pretreatment temperature is between about 180° C. and about 230° C., and the residence time in the pretreatment reactor is between seconds and hours (e.g., between about 10 seconds and about 120 minutes).

In another embodiment, the pretreatment 10 comprises an ammonia fiber expansion (AFEX), which is a type of alkali pretreatment, and which may produce little or no monosaccharides. In the AFEX process, the biomass is contacted with ammonia or ammonium hydroxide, which is typically concentrated, in a pressure vessel. The contact is maintained for a sufficient time to enable the ammonia or ammonium hydroxide to swell (i.e., decrystallize) the cellulose fibers. The pressure is then rapidly reduced which allows the ammonia to flash or boil and explode the cellulose fiber structure. The flashed ammonia may then be recovered according to known processes. The AFEX process may be run at about 60° C. to about 160° C. The duration of this pretreatment may vary from minutes to hours (e.g., may be between about 1 minute and about 20 minutes).

In each of the above-described embodiments wherein the pretreatment 10 includes the addition of steam, the steam under high pressure may penetrate the biomass structure and wet the material. If the pressure in the reactor is rapidly released (e.g., at the end of the predetermined residence time in the pretreatment reactor), the wet biomass may "explode", thereby providing a pretreated biomass having a substantially mulched and/or disrupted structure. Notably, the expansion of the water vapour and/or the reaction of the biomass with water at elevated temperatures provides both a mechanical and chemical breakdown of the biomass structure. In addition, the sudden release of pressure from the steam explosion may result in the pretreated material being rapidly discharged from the pretreatment reactor (e.g., via a blow-out valve).

In general, any pretreatment reactor that provides the conditions for pretreatment may be used. In one embodiment, the pretreatment reactor is a vertical reactor, a horizontal reactor, or an inclined reactor. In one embodiment, the pretreatment reactor is a vertical reactor and includes a rotary sweeper (not shown) that conveys the heated biomass to a screw conveyor so that it can be discharged via a blow-out valve. In one embodiment, the pretreatment reactor is a horizontal reactor that includes a screw conveyor that leads the heated biomass to the blow-out valve. In one embodiment, the pretreatment reactor is a horizontal reactor and the biomass to be treated therein has a consistency between about 17 wt % and about 67 wt %. In one embodiment, the pretreatment is conducted in one or more pretreatment reactors.

In embodiments wherein biomass having a consistency between about 17 wt % and about 67 wt % is fed to the pretreatment reactor, and wherein the pretreatment 10 does not significantly breakdown the cellulose component of the biomass (e.g., although some or all of the hemicellulose component may be hydrolyzed), the biomass discharged from the pretreatment reactor may have a relatively high consistency (e.g., greater than about 15 wt % or even greater than about 20 wt %) and may be relatively hot (e.g., at a temperature greater than about 100° C. and more commonly greater than about 140° C.).

Cooling

In general, the relatively hot, pretreated biomass may need to be cooled, in one or more steps, prior to the biological conversion 50. For example, the pretreated biomass may need to be cooled from the pretreatment temperature (e.g., which may be as high as about 300° C., or more commonly less than about 240° C.) to a temperature that is compatible with the microorganisms(s) used in the subsequent biological conversion 50. For example, enzymes used in cellulose hydrolysis may have optimum temperature for activity ranges between about 20° C. and about 80° C., and more commonly between about 40° C. and about 60° C., whereas ethanol producing yeast strains, which may be used to ferment the sugars, often have an optimal fermentation temperature between about 28° C. and about 40° C. In one embodiment, the relatively hot, pretreated biomass is cooled to a temperature between about 45° C. and about 55° C. In one embodiment, the relatively hot, pretreated biomass is cooled to about 50° C., which is the optimal temperature for one commonly available cellulase.

Referring again to FIG. 1, the pretreated biomass discharged from the pretreatment reactor may be cooled when it is mixed with a cooling liquid in the mixing stage 20. In general, the mixing stage 20 may utilize one or more vessels, wherein at least one vessel has an agitator for mixing the cooling liquid with the pretreated biomass, thus forming a cooled slurry. The term agitator, as used herein, refers to any device, component, and/or agitation means that puts at least a portion of the cooling liquid and/or pretreated biomass in motion in order to allow mixing. For example, some means of providing agitation include mechanical stirring, gas injection, and hydraulic mixing. Some examples of suitable agitators and/or vessels that include an agitator include impellers (e.g., axial-flow impeller, radial-flow impeller, or mixed flow impeller), a rotating stirrer (e.g., including a propeller, paddles, flat blade turbine, pitched blade turbine, and/or vanes), tumbling stirrer, and eductors. In one embodiment, the agitator and/or vessel that includes the agitator is a turbulent mixer. In another embodiment, the agitator is a laminar mixer (e.g., anchor impeller). Optionally, the vessel includes one or more baffles.

Advantageously, sufficient cooling liquid and/or other liquids may be added in a mixing zone of the vessel such that the cooled slurry exiting the vessel has a consistency that facilitates pumping of the cooled slurry within the system (e.g., less than about 12 wt %). For example, in one embodiment, the consistency of the cooled slurry is about 8%. In one embodiment, a pump, such as a centrifuge pump, is used to pump the cooled slurry up in elevation (e.g., to an elevation above an inlet to a hydrolysis and/or fermentation tank in the biological conversion 50). More specifically, the pump is used to transport the cooled slurry up to a solid-liquid separation 30.

In general, the solid-liquid separation 30 may utilize any apparatus, device and/or system that separates at least a portion of the liquid in the slurry from the solids in the slurry. In one embodiment, the solid-liquid separation 30 utilizes one or more apparatuses that separate liquids and solids using gravity and/or centrifugal forces. For example, in one embodiment, the solid-liquid separation uses one or more decanter centrifuges. Decanter centrifuges, which are based on an accelerated settling of solids due to centrifugal acceleration, may be advantageous over other solid-liquid separators because they may provide a relatively quick and easy separation, may have relatively high throughput, and may be operated in continuous mode. Moreover, decanter centrifuges have been found to be particularly efficient at dewatering pretreated biomass, and in particular, more efficient than conventional solid-liquid separation devices such as plate/frame filter presses, belt filter presses, and screw presses. For example, it has been found that pretreated biomass, and in particular, steam pretreated biomass, which may have a relatively muddy consistency, may clog conventional solid-liquid separators that rely on a physical separation between the solid and liquids phases (e.g., such as filter presses). In addition, using a decanter centrifuge for the solid-liquid separation may be advantageous since these devices may be designed to continuously provide a first stream comprising a liquid component of the slurry (e.g., often termed centrate) and a second other stream comprising a solid component of the slurry (e.g., often termed wet cake). Further advantageously, decanter centrifuges, which may use a combination of drainage and compression, may be designed to provide wet cake having a consistency between about 15 wt % and about 40 wt %. Moreover, in operation, the decanter centrifuge may be used to provide wet cake having varying consistency by adding centrate to the wet cake, thus further improving the flexibility.

The wet cake is fed to an inlet of a reactor in the biological conversion (e.g., a hydrolysis reactor and/or a fermentation reactor). Optionally, enzymes are mixed into the wet cake prior to entering the biological conversion reactor and/or directly into the biological conversion reactor. The enzymes may be handled in an aqueous solution or as a powder or granulate.

At least a portion of the centrate is recycled back to the vessel after being cooled in the cooling system 40. In one embodiment, the cooling system 40 includes one or more devices that actively cool the centrate. Actively cooling the centrate advantageously allows the temperature of the cooled centrate to be adjusted as required, and more specifically, adjusted such that the temperature and/or consistency of the cooled slurry is within a predetermined range. For example, if it is desired that the cooled slurry have a consistency of about 8 wt % and temperature of about 50° C., and if it is determined that a predetermined volume of centrate will provide the approximately 8 wt % consistency, then the cooling system may cool the centrate to a temperature that would allow the predetermined volume of centrate to cool the biomass to about 50° C.

In general, the consistency of the cooled slurry is dependent on the temperature and consistency of the pretreated biomass discharged into the vessel and the temperature of the cooled centrate. For pretreated biomass having a consistency that is between about 15% and about 25% and a temperature of about 100° C., it may be advantageous to cool the centrate to between about 25° C. and about 35° C. For example, for pretreated biomass having a temperature of about 100° C. and a consistency of about 20 wt %, cooling the centrate to about 30° C. may advantageously provide a slurry having a temperature of about 50° C. and a consistency of about 8%. By comparison, cooling the centrate only to about 35° C., may decrease the consistency to about 6 wt %. Notably, slurries having a consistency that is less than about 6 wt % may increase the hydraulic load on the decanter centrifuge (e.g., or other solids-liquid separator).

In one embodiment, the centrate is cooled to between about 0° C. and about 85° C. In another embodiment, the centrate is cooled to between about 10° C. and about 60° C. In another embodiment, the centrate is cooled to between about 20° C. and about 50° C., or between about 20° C. and about 40° C. In another embodiment, the centrate is cooled to between about 25° C. and about 35° C. In another embodiment, the centrate is cooled to about 30° C.

In one embodiment, the cooled slurry has a consistency between about 4 wt % and about 15 wt %. In another embodiment, the cooled slurry has a consistency between about 5 wt % and about 12 wt %. In another embodiment, the cooled slurry has a consistency between about 6 wt % and about 10 wt %. In one embodiment, the cooled slurry has a consistency between about 7.5 wt % and about 8.5 wt %. In one embodiment, the cooled slurry has a consistency of about 8 wt %. Providing a cooled slurry having a consistency less than about 12 wt %, and in particular between about 6 wt % and about 10 wt % may be advantageous in that it provides a reasonable compromise between pumpability, cooling, amount of biomass transferred per unit volume of slurry, and liquid capacity of decanter centrifuges. Although providing a slurry having a consistency between about 5 and about 12 wt % may have some economic advantages, other advantages of the cooling loop may be realized even when the consistency of the slurry is outside this range.

In one embodiment, the cooling system 40 includes one or more industrial cooling systems that are able to cool the liquid component. In one embodiment, the cooling system 40 includes one or more heat exchangers. For example, in one embodiment, the cooling system includes a shell and tube heat exchanger, a plate-and-frame heat exchanger, and/or a liquid-liquid heat exchanger. If more than one heat exchanger is used, they may be configured in parallel or in series. In one embodiment, the heat exchanger uses cooling tower water. In another embodiment, the heat exchanger uses chilled water that has been mechanically cooled. In another embodiment, the cooling system 40 includes one or more direct refrigerant systems. In one embodiment, the cooling system 40 includes a combination of cooling devices and/or mechanisms. For example, in one embodiment, the cooling system includes one or more heat exchangers that use cooling tower water, one or more heat exchangers that use chilled water, one or more heat exchangers that use chilled cooling tower water, and/or one or more direct refrigerant systems.

In one embodiment, the cooled slurry and/or the centrate are conveyed through the system using one or more pumps and/or conduits. Advantageously, the pumps and/or conduits may include pumps and/or pipes commonly used to transport slurries having a consistency less than about 12 wt %.

In one embodiment the pump(s), piping, decanter(s,), and heat exchanger(s) are formed from a low alloy material, such as 304 grade stainless steel.

In one embodiment, the cooling system 40 includes one or more inlets for introducing a pH adjusting chemical to the biomass. For example, in one embodiment, wherein the pretreatment is an acid pretreatment, the pH adjusting chemical may be an alkali and/or a base such as potassium hydroxide, sodium hydroxide, ammonium hydroxide, calcium hydroxide, ammonia gas, calcium carbonate, potassium carbonate, or any mixtures thereof in one embodiment, the pH adjusting chemical includes one or more buffers. In one embodiment, wherein the pretreatment is an alkali pretreatment, the pH adjusting chemical may be an acid such as sulfuric acid.

In one embodiment, sufficient pH adjusting chemical is added to bring the pH of the cooled slurry to a value at which enzyme(s) in a subsequent hydrolysis has reasonable activity. In general, the pH at which an enzyme is compatible depends on the particular enzyme(s) utilized in the cellulose hydrolysis, and may be determined readily by those of skill in the art. For example, many cellulases may have an optimum pH range between about 4 and about 7, and often about 5. In one embodiment, sufficient pH adjusting chemical is added to bring the pH of the biomass slurry to between about 4 and about 8. In another embodiment, sufficient pH adjusting chemical is added to bring the pH of the biomass slurry to between about 4.5 and about 6.

In one embodiment, the one or more inlets for introducing the pH adjusting chemical to the biomass are in fluid communication with one or more pipes used to transport the cooled centrate such that the pH adjusting chemical is mixed into the cooling liquid and then added to the vessel. In another embodiment, the one or more inlets for introducing the pH adjusting chemical to the biomass are in fluid communication with the vessel such that the pH adjusting chemical and cooled centrate are added separately (although optionally simultaneously) to the biomass. In each case, the agitator and/or cooling liquid advantageously make it possible to provide uniform and consistent mixing (e.g., within a mixing zone of the vessel). Accordingly, problems associated with mixing a pH adjusting chemical with high consistency biomass are obviated.

In one embodiment, enzyme is added to the cooled and pH adjusted slurry. In one embodiment, enzyme is added downstream of the vessel (e.g., upstream or downstream of the solid-liquid separation 30). Optionally, the enzyme is dispersed in the solid component with a dedicated mixer (e.g., a high consistency mixer). In general, the enzyme may be added to the biomass in solid or liquid form. In one embodiment, enzyme addition is carried out by adding enzyme to a reservoir, such as a tank, to form an enzyme solution, which is then introduced to the solids component of the slurry fed to the biological conversion 50. Optionally, enzyme is introduced to the solids component of the slurry fed to the biological conversion 50 via chemical injection quills or through appropriately sized tubing or via a pipe. In one embodiment, a first dose of enzyme is added to the cooled slurry upstream of the solid-liquid separation 30, and a second dose of enzyme is added to the stream comprising the solids from the solid-liquid separation 30. In one embodiment, the enzyme includes cellulose at a total dosage between about 1.0 to about 40.0 Filter Paper Units (FPU or IU) per gram of cellulose or between about 2 to about 20 mg protein per gram cellulose, Optionally, the enzyme is a mixture of enzymes. In one embodiment, the enzyme solution is prepared using excess centrate provided by the decanter. Advantageously, enzyme addition to much the larger volume centrate stream offers excellent dispersion into decanter cake.

As described above, in one embodiment, sufficient cooling liquid may be added in the mixing stage 20 to cool pretreated biomass having a consistency of about 20 wt % and a temperature of about 100° C. to about 50° C. (e.g., and provide a cooled slurry having a consistency of about 8 wt %). However, as also described above, in many embodiments, the pretreatment 10 will be conducted at temperatures above 100° C. (e.g., up to 300° C., and often between about 180° C. and about 240° C.). In these embodiments, the biomass may be cooled from the pretreatment temperature (e.g., which is typically greater than 100° C., one more typically greater than about 140° C.) to about 100° C. via one or more flashing steps. For example, in one embodiment, the pretreatment includes a steam explosion.

Figure 2:
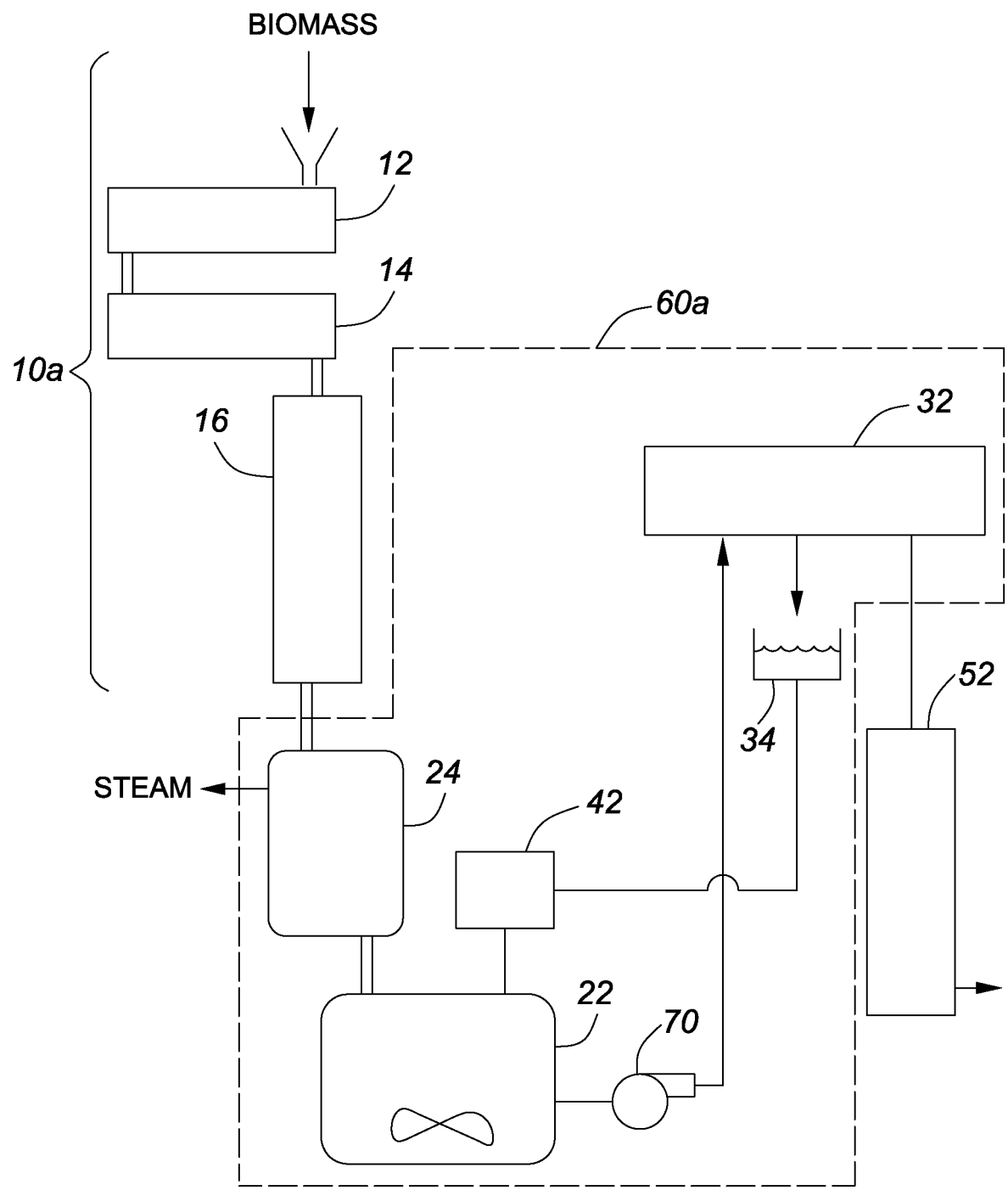
FIG. 2 is a schematic diagram showing a system for hydrolyzing biomass in accordance with one embodiment of the instant invention.

In one embodiment, pretreatment 10 is provided with a pretreatment system 10a. Referring to FIG. 2, the pretreatment system 10a includes a pressurized dewatering system 12, an optional heating chamber 14, and a pretreatment reactor 16. Although illustrated as three separate components for demonstrative purposes, it should be understood that the pretreatment system may include these and/or other components, which may be provided as one or more separate components and/or as integrated components. For example, in one embodiment, the pretreatment system 10a includes one of the pretreatment systems described in US Publ. Nos. 2010/0056774 and/or 2013/0071903, which are hereby incorporated by reference.

Referring again to FIG. 2, the biomass is pumped as an aqueous slurry (e.g., having a consistency of about 1 wt % to about 12 wt %, and more commonly between about 5 wt % to about 7 wt %) to the pressurized dewatering system 12. The pressurized dewatering system may include a predraining zone (not shown), wherein at least some of the water is removed and fed to a high pressure pump (now shown), which creates a high pressure zone for further dewatering. The pressurized dewatering system 12 reduces the moisture content of the biomass to an amount suitable for pretreatment. For example, in one embodiment, the pressurized dewatering system 12 includes a pressurized dewatering press or a pressurized plug screw feeder (e.g., as described in US Publ. No. 2010/0056774). In one embodiment, the pressured dewatering system 12 is at a pressure between about 70 psia and about 800 psia. The dewatered biomass (e.g., which may or may not be in plug form and may have a consistency between about 20 wt % and about 67 wt %), may then be fed to the optional heating chamber 14, as for example, described in US Publ. No. 2013/0071903, and then to the pretreatment reactor 16. A pretreatment chemical, if used, may be added in the pressurized dewatering system 12, in the heating chamber 14, and/or directly into the pretreatment reactor 16. For example, in one embodiment, an acid pretreatment chemical is added to the biomass upstream of the inlet of a pressurized screw press, at the inlet to a pressurized screw press, in a dewatering zone of a pressurized screw press, in the pressurized plug screw feeder, and/or in the reaction zone of the pretreatment reactor. The pretreatment chemical may be added in gaseous and/or liquid form.

The pretreatment reactor 16, which for exemplary purposes is shown as a vertical reactor, may be any reactor that may contain the biomass while the biomass is subject to at least a portion of the pretreatment. For example, in one embodiment the pretreatment reactor is a vertical reactor, such as an upflow or downflow vertical reactor. In another embodiment, the pretreatment reactor is a horizontal or inclined reactor. The pretreatment reactor 16 may be equipped with an internal mechanism, such as a screw, conveyor, or similar mechanism, for conveying the lignocellulosic feedstock within a reactor zone of the pretreatment reactor.

In one embodiment, the pretreatment reactor includes one or more inlets for injecting steam into the biomass. Accordingly, the pretreatment reactor may be held at a predetermined temperature and/or pressure. For example, in one embodiment the one or more inlets for injecting steam are provided near the reactor zone of the pretreatment reactor 16.

In general, the biomass will be treated in the pressurized pretreatment reactor 16 at an elevated temperature (e.g., above 100° C.) for a specific amount of time. Optionally, the biomass is treated under acidic or basic conditions via the addition of one or more pretreatment chemicals. The temperature, pressure, and/or residence time of the biomass in the reaction zone may depend upon a number of variables, including the pH in the reaction zone and the degree, if any, to which hydrolysis of the polysaccharides is desired. For example, in one embodiment, wherein the pretreatment is an acid pretreatment, the biomass may have a residence time in the pretreatment reactor from about 10 seconds to about 20 minutes, or about 10 seconds to about 600 seconds, or about 10 seconds to about 180 seconds. The maximum temperature may be between about 150° C. to about 280° C. The pH for the pretreatment may be between about 0.5 and about 3, or between about 1.0 and about 2.0. Notably, the partially dewatered lignocellulosic feedstock may be heated prior to its entry into the reaction zone (e.g., in the optional heating chamber 14), in the reaction zone, or a combination thereof.

When the biomass has been resident in the reactor zone of the pretreatment reactor 16 for a predetermined time, the treated biomass is then discharged into a flash tank 24 to provide the pretreated biomass. Since the flash tank 24 is held at a pressure that is lower than the pressure of the pretreatment reactor 16, the temperature of the pretreated biomass will drop from the pretreatment temperature to a. temperature dependent on the pressure in the flash tank. For example, if the flash tank is at about atmospheric pressure, the pretreated biomass temperature will be about 100° C., If the flash tank is below atmospheric pressure, the temperature will be lower than 100° C. if the flash tank is held above atmospheric pressure, the temperature will be greater than 100° C. Advantageously, utilizing pressures that provide temperatures that are about 100° C. ±10° C. allows reasonable amounts of cooling water to be used. In one embodiment, the flash tank is held at about 5 psig. Since this overpressure results in a higher pretreated biomass temperature, the temperature of the cooling water and/or the amount of cooling water added (i.e., and thus output consistency) may be adjusted to provide the desired slurry temperature.

In general, the pretreated biomass may have a consistency between about 15 wt % and about 40 wt % upon entering the flash tank. For example, in one embodiment, the pretreated biomass has a consistency of about 20%.

The cooled pretreated biomass (e.g., having a consistency between about 15 wt % and about 40 wt % and a temperature of about 100° C.) is then fed to a vessel 22, which is in fluid communication with the flash tank 24. The vessel 22, which contains a cooling liquid, has an agitator for mixing the cooled pretreated biomass with the cooling liquid in order to further cool the biomass and to reduce the viscosity thereof. In one embodiment, the vessel 22 contains sufficient water to cool the pretreated biomass to a temperature that is compatible with enzymes for converting the pretreated biomass to a transportation fuel and/or other product. For example, in one embodiment, the vessel contains sufficient water to produce a cooled slurry at an outlet thereof having a temperature that is less than about 70° C. and a consistency that is between about 5 wt % and about 12 wt %. For example, in one embodiment, a cooled slurry having a temperature of about 50° C. and a consistency of about 8 wt % is provided.

The cooled slurry is transported via centrifugal pump 70 up to a solid-liquid separation system, which includes a decanter centrifuge 32.

The decanter centrifuge 32 separates the cooled slurry into a first stream comprising a liquid component of the slurry (e.g., the centrate) and a second other stream comprising a solid component of the slurry (e.g., the wet cake). In one embodiment, the decanter centrifuge provides the two streams on a substantially continuous basis. In one embodiment, the decanter centrifuge removes sufficient liquid from the slurry that the wet cake has a consistency between about 15 wt % and about 40 wt %. For example, in one embodiment, the wet cake has a consistency of about 20%.

The wet cake is fed to an inlet of a reactor 52 in the biological conversion e.g., a hydrolysis reactor and/or a fermentation reactor). Optionally, enzymes are mixed into the wet cake prior to entering the biological conversion reactor and/or directly into the biological conversion reactor.

The centrate is recycled back to the vessel 22 after being cooled in the cooling system, which includes a cooling device 42, In one embodiment, the cooling device 42 includes a heat exchanger (e.g., a shell and tube heat exchanger, a plate-and-frame heat exchanger, or a liquid-liquid heat exchanger), which is used to actively cool the centrate to a predetermined temperature. In one embodiment, the centrate is cooled to below about 60° C. In another embodiment, the centrate is cooled to below about 35° C. In one embodiment, the centrate is cooled to about 30° C. Optionally, the centrate is collected in a centrate tank 34 prior to being fed to the cooling device 42. In one embodiment, the cooled slurry from the vessel 22 is pumped to and fed into a plurality of decanter centrifuges (e.g., operating in parallel), and the centrate from each decanter in the plurality is fed to the centrate tank 34. In this embodiment, the vessel 22, flash tank 24, decanter centrifuge 32, centrate tank 34, cooling device 42, and pump 70 are all part of a cooling system 60a used to cool and/or transport the biomass prior to the biological conversion 50.

Figure 3:
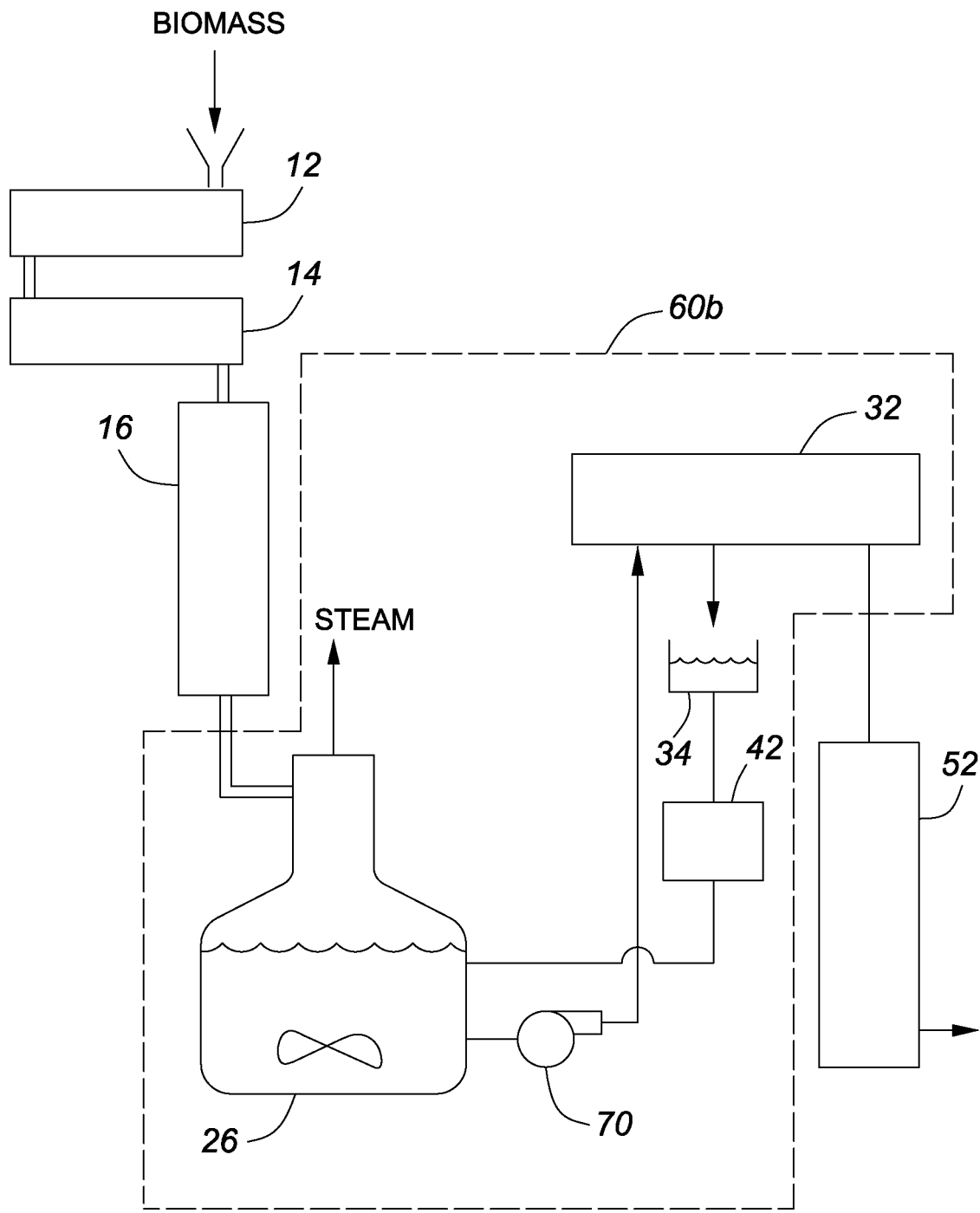
FIG. 3 is a schematic diagram showing a system for hydrolyzing biomass in accordance with another embodiment of the instant invention.

Referring to FIG. 3, there is shown another embodiment of a cooling system for cooling and/or transporting the biomass prior to the biological conversion 50. The biomass is pumped as an aqueous slurry (e.g., having a consistency of about 1 wt % to about 10 wt %, and more commonly between about 5 wt % to about 7 wt %) to the pressurized dewatering system 12, which reduces the moisture content of the biomass to an amount suitable for pretreatment. For example, in one embodiment, the pressurized dewatering system 12 includes a pressurized dewatering press or a pressurized plug screw feeder (e.g., as described in US Publ. No. 2010/0056774). In one embodiment, the pressured dewatering system 12 is at a pressure between about 70 psia and about 800 psia. The dewatered biomass (e.g., which may or may not be in plug form and may have a consistency between about 20 wt % and about 67 wt %), may then be fed to the optional heating chamber 14, as for example, described in US Publ. No. 2013/0071903, and then to the pretreatment reactor 16. A pretreatment chemical, if used, may be added in the pressurized dewatering system 12, in the heating chamber 14, and/or directly into the pretreatment reactor 16. For example, in one embodiment, an acid pretreatment chemical is added to the biomass upstream of the inlet of a pressurized screw press, at the inlet to a pressurized screw press, in a dewatering zone of a pressurized screw press, in the pressurized plug screw feeder, and/or in the reaction zone of the pretreatment reactor. The pretreatment chemical may be added in gaseous and/or liquid form.

The pretreatment reactor 16, which for exemplary purposes is shown as a vertical reactor, may be any reactor that may contain the biomass while the biomass is subject to at least a portion of the pretreatment. For example, in one embodiment the pretreatment reactor is a vertical reactor, such as an upflow or downflow vertical reactor. In another embodiment, the pretreatment reactor is a horizontal or inclined reactor. The pretreatment reactor 16 may be equipped with an internal mechanism, such as a screw, conveyor, or similar mechanism, for conveying the lignocellulosic feedstock within a reactor zone of the pretreatment reactor.

In one embodiment, the pretreatment reactor includes one or more inlets for injecting steam into the biomass. Accordingly, the pretreatment reactor may be held at a predetermined temperature and/or pressure. For example, in one embodiment the one or more inlets for injecting steam are provided near the reactor zone of the pretreatment reactor 16.

In general, the biomass will be treated in the pressurized pretreatment reactor 16 at an elevated temperature (e.g., above 100° C.) for a specific amount of time. Optionally, the biomass is treated under acidic or basic conditions via the addition of one or more pretreatment chemicals. In fact, the temperature, pressure, and/or residence time of the biomass in the reaction zone may depend upon a number of variables, including the pH in the reaction zone and the degree, if any, to which hydrolysis of the polysaccharides is desired. For example, in one embodiment, wherein the pretreatment is an acid pretreatment, the biomass may have a residence time in the pretreatment reactor from about 10 seconds to about 20 minutes, or about 10 seconds to about 600 seconds, or about 10 seconds to about 180 seconds. The maximum temperature may be between about 150° C. to about 280° C. The pH for the pretreatment may be between about 0.5 and about 3, or between about 1.0 and about 2.0. Notably, the partially dewatered lignocellulosic feedstock may be heated prior to its entry into the reaction zone (e.g., in the optional heating chamber 14), in the reaction zone, or a combination thereof.

When the biomass has been resident in the pretreatment reactor 16 for a predetermined time, the treated biomass is then discharged into a flash tank 26 to provide the pretreated biomass. Since the flash tank 26 is held at a pressure that is lower than the pressure of the pretreatment reactor 16, the temperature of the pretreated biomass will drop from the pretreatment temperature to a temperature dependent on the pressure of the flash tank. For example, if the flash tank is at about atmospheric pressure, the pretreated biomass temperature will be about 100° C. The pretreated biomass may have a consistency between about 15 wt % and about 40 wt % upon discharge into the flash vessel 26. For example, in one embodiment, the pretreated biomass has a consistency of about 20 wt %.

The flash vessel 26, which contains a cooling liquid, has an agitator for mixing the pretreated biomass (e.g., having a temperature of about 100° C. and a consistency between about 15 wt % and about 40 wt % upon immediate discharge into said vessel) with the cooling liquid in order to further cool the biomass and to reduce the viscosity thereof. More specifically, the agitator provides a mixed dilution zone that operates at a predetermined consistency (e.g., operates at a consistency that is less than about 12 wt %). In one embodiment, the flash vessel 26 contains sufficient water to cool the pretreated biomass to a temperature that is compatible with enzymes for converting the pretreated biomass to a transportation fuel and/or other product. In one embodiment, the vessel contains sufficient water to produce a cooled slurry at an outlet thereof having a temperature that is less than about 70° C. and a consistency that is between about 5 wt % and about 12 wt %. For example, in one embodiment, a cooled slurry having a temperature of about 50° C. and a consistency of about 8 wt % is provided. In one embodiment, the liquid used to cool the biomass and to reduce the consistency has been cooled by the cooling device 42 and has had pH adjusting chemicals (e.g., neutralizing chemicals) added there to so that the slurring in the mixed zone is at about 5 pH and about 50° C. In one embodiment, the biomass has a retention time in the order of about 5 minutes in the mixed zone.

The cooled slurry is discharged from an outlet of the flash vessel 26 and is pumped to a higher vertical elevation via a conventional centrifugal pump 70 and standard piping sized for the relatively low viscosity cooled slurry (e.g., having a consistency less than about 12 wt %).

In one embodiment, the decanter centrifuge 32 thickens the cooled slurry back to a minimum of about 15 wt %. For example, in one embodiment, the decanter centrifuge 32 thickens the cooled slurry back to at least about 18 wt %. in one embodiment, the decanter centrifuge 32 thickens the cooled slurry back to at least about 20 wt %. In one embodiment, the volume of centrate collected is equal to or greater than the volume of liquid necessary to cool the pretreated biomass from about 100° C. to a temperature compatible with the biological conversion 50. Although the centrate may be high in C5 sugars, it should be noted that since the cooling system 60b may be a substantially closed loop system, the C5 sugar yield will not be substantially affected by the cooling system 60b (i.e., once the system has achieved steady state operation). Advantageously, in embodiments wherein the solid-liquid separation is provided by the decanter centrifuge 32, the centrate will have only a minimal amount of UDS fines (i.e., small fibrous elements). Accordingly, the centrate may be cooled efficiently with a conventional heat exchanger designed for low UDS slurries (e.g., in embodiments wherein the cooling device 42 includes a heat exchanger).

In one embodiment, any excess centrate may be used to reduce the consistency of the wet cake so that it is suitable for the biological conversion and/or to provide an enzyme solution for the biological conversion.

Advantageously, the flash tank 26 provides cooling of the biomass from the pretreatment temperature to a temperature compatible with microorganisms used in the biological conversion 50 without using a vacuum flash tank and without diluting the biomass to a point that the hydraulic load of the decanter centrifuges is exceeded. More specifically, the combination of using an atmospheric flash tank and cooling water cooled below about 50° C. provides maximum cooling with minimal water without the expense of using a vacuum flash.

Moreover, the use of the cooling system 60b provides the means to cool the pretreated biomass without washing. More specifically, the system is more flexible with regards to whether the C5 sugars and/or other pretreatment sugars are removed via a washing and processed separately, or whether they remain with the solids. For example, in one embodiment, a washing step is integrated with the solid-liquid separation.

Figure 4:
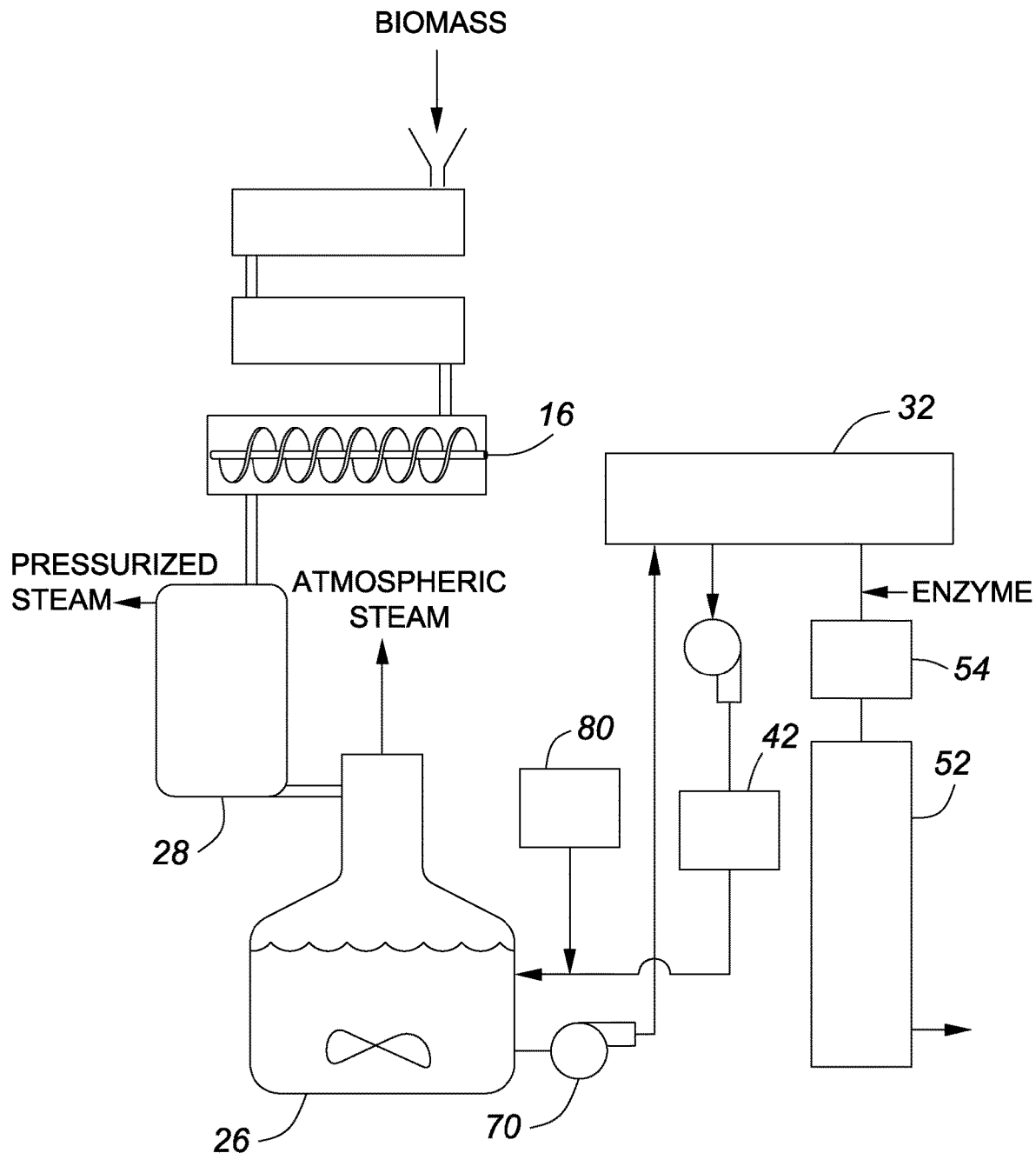
FIG. 4 is a schematic diagram showing a system for hydrolyzing biomass in accordance with yet another embodiment of the instant invention.

Referring to FIG. 4, there is shown another embodiment of a cooling system for cooling and/or transporting the biomass prior to the biological conversion 50. The biomass is pumped as an aqueous slurry (e.g., having a consistency of about 1 wt % to about 12 wt %, and more commonly between about 5 wt % to about 7 wt %) to the pressurized dewatering system 12, which reduces the moisture content of the biomass to an amount suitable for pretreatment. For example, in one embodiment, the pressurized dewatering system 12 includes a pressurized dewatering press or a pressurized plug screw feeder (e.g., as described in US Publ. No. 2010/0056774). In one embodiment, the pressured dewatering system 12 is at a pressure between about 70 psia and about 800 psia. The dewatered biomass (e.g., which may or may not be in plug form and may have a consistency between about 20 wt % and about 67 wt %), may then be fed to the optional heating chamber 14, as for example, described in US Publ. No. 2013/0071903, and then to the pretreatment reactor 16. A pretreatment chemical, if used, may be added in the pressurized dewatering system 12, in the heating chamber 14, directly into the pretreatment reactor 16, and/or at any point upstream of the pretreatment reactor 16. For example, in one embodiment, an acid pretreatment chemical is added to the biomass upstream of the inlet of a pressurized screw press, at the inlet to a pressurized screw press, in a dewatering zone of a pressurized screw press, in the pressurized plug screw feeder, and/or in the reaction zone of the pretreatment reactor. The pretreatment chemical may be added in gaseous and/or liquid form.

The pretreatment reactor 16, which for exemplary purposes is shown as a horizontal reactor, may be any reactor that may contain the biomass while the biomass is subject to at least a portion of the pretreatment. For example, in another embodiment the pretreatment reactor is a vertical reactor, such as an upflow or downflow vertical reactor. In another embodiment, the pretreatment reactor is an inclined reactor. The pretreatment reactor 16 may be equipped with an internal mechanism, such as a screw, conveyor, or similar mechanism, for conveying the lignocellulosic feedstock within a reactor zone of the pretreatment reactor.

In one embodiment, the pretreatment reactor 16 includes one or more inlets for injecting steam into the biomass. Accordingly, the pretreatment reactor may be held at a predetermined temperature and/or pressure. For example, in one embodiment the one or more inlets for injecting steam are provided near the reactor zone of the pretreatment reactor 16.

In general, the biomass will be treated in the pressurized pretreatment reactor 16 at an elevated temperature (e.g., above 100° C.) for a specific amount of time. Optionally, the biomass is treated under acidic or basic conditions via the addition of one or more pretreatment chemicals. The temperature, pressure, and/or residence time of the biomass in the reaction zone may depend upon a number of variables, including the pH in the reaction zone and the degree, if any, to which hydrolysis of the polysaccharides is desired. For example, in one embodiment, wherein the pretreatment is an acid pretreatment, the biomass may have a residence time in the pretreatment reactor from about 10 seconds to about 20 minutes, or about 10 seconds to about 600 seconds, or about 10 seconds to about 180 seconds. The maximum temperature may be between about 150° C. to about 280° C. The pH for the pretreatment may be between about 0.5 and about 3, or between about 1.0 and about 2.0. Notably, the partially dewatered lignocellulosic feedstock may be heated prior to its entry into the reaction zone (e.g., in the optional heating chamber 14), in the reaction zone, or a combination thereof.

When the biomass has been resident in the pretreatment reactor 16 for a predetermined time, the treated biomass is then discharged into the first flash tank 28 of a plurality of flash tanks. Since the first flash tank 28 is held at a pressure that is lower than the pressure of the pretreatment reactor 16, but higher than the pressure of the second flash tank 26, the temperature of the treated biomass will drop as it passes from the pretreatment reactor 16 to the first flash tank 28, to the second flash tank 26. For example, in one embodiment, the pretreatment reactor is held at a first pressure (e.g., between about 90 psig and about 800 psig), the first flash tank 28 is held at a second lower pressure (e.g., between about 10 psig and about 90 psig), and the second flash tank is held at a third lower pressure (e.g., at or near atmospheric pressure (e.g., about 0 psig)). Advantageously, providing a plurality of flash tanks arranged in series wherein the pressure decreases along the series may provide better steam recovery and/or recycling. For example, in one embodiment, low pressure steam recovered from the first flash tank 28 is used elsewhere in the process (e.g., in evaporation or distillation steps), while the second flash tank is provided with a scrubber.

In embodiments wherein the second flash tank 26 is at atmospheric pressure, the temperature of the pretreated biomass discharged directly therein may be about 100° C. In one embodiment, this pretreated biomass may have a consistency between about 15 wt % and about 40 wt %. For example, in one embodiment, the pretreated biomass has a consistency of about 20% upon discharge into the flash vessel 26.

The flash vessel 26, which contains a cooling liquid, has an agitator for mixing the pretreated biomass (e.g., having a temperature of about 100° C. and a consistency between about 15 wt % and about 40 wt % upon immediate discharge into said vessel) with the cooling liquid in order to further cool the biomass and to reduce the viscosity thereof. More specifically, the agitator provides a mixed dilution zone that operates at a predetermined consistency (e.g., operates at a consistency that is less than about 12 wt %). In one embodiment, the flash vessel 26 contains sufficient water to cool the pretreated biomass to a temperature that is compatible with enzymes for converting the pretreated biomass to a transportation fuel and/or other product. In one embodiment, the vessel contains sufficient water to produce a cooled slurry at an outlet thereof having a temperature that is less than about 70° C. and a consistency that is between about 5 wt % and about 12 wt %. For example, in one embodiment, a cooled slurry having a temperature of about 50° C. and a consistency of about 8 wt % is provided. In one embodiment, the liquid used to cool the biomass and to reduce the consistency has been cooled by the cooling device 42 and has had pH adjusting chemicals (e.g., neutralizing chemicals) added there to so that the slurry in the mixed zone is at about 5 pH and about 50° C. In one embodiment, the biomass has a retention time in the order of about 5 minutes in the mixed zone.

The cooled slurry is discharged from an outlet of the flash vessel 26 and is pumped to a higher vertical elevation via a conventional centrifugal pump 70 and standard piping sized for the relatively low viscosity cooled slurry (e.g., having a consistency less than about 12 wt %).

The decanter centrifuge 32 thickens the cooled slurry back to a minimum of 15 wt %. More specifically, the decanter centrifuge 32 separates the cooled slurry into a first stream comprising a liquid component of the slurry (e.g., the centrate) and a second other stream comprising a solid component of the slurry (e.g., the wet cake). In one embodiment, the decanter centrifuge provides the two streams on a substantially continuous basis. In one embodiment, the decanter centrifuge removes sufficient liquid from the slurry that the wet cake has a consistency between about 15 wt % and about 40 wt %. For example, in one embodiment, the wet cake has a consistency of at least about 18%. In one embodiment, the wet cake has a consistency of at least about 20 wt %. In one embodiment, the wet cake has a consistency of about 28 wt %.

The wet cake is fed to an inlet of a reactor 52 in the biological conversion (e.g., a hydrolysis reactor and/or a fermentation reactor). Optionally, enzymes are mixed into the wet cake prior to entering the biological conversion reactor and/or directly into the biological conversion reactor. In one embodiment, enzymes are mixed into the wet cake with a mixer 54.

The centrate is recycled back to the flash tank 26 after being cooled in the cooling system, which includes a cooling device 42. In one embodiment, the cooling device 42 includes a heat exchanger (e.g., a shell and tube heat exchanger, a plate-and-frame heat exchanger, or a liquid-liquid heat exchanger), which is used to actively cool the centrate to a predetermined temperature. In one embodiment, the centrate is cooled to below about 60° C. In another embodiment, the centrate is cooled to below about 35° C. In one embodiment, the centrate is cooled to about 30° C. Optionally, the centrate is collected in a centrate tank (not shown) prior to being fed to the cooling device 42. In one embodiment, the cooled slurry from the flash tank 26 is pumped to and fed into a plurality of decanter centrifuges (e.g., operating in parallel), and the centrate from each decanter in the plurality is fed to the centrate tank. In this embodiment, the flash tank 26, decanter centrifuge 32, centrate tank (now shown), cooling device 42, and pump 70 are all part of a cooling system used to cool and/or transport the biomass prior to entering the biological conversion reactor 52.

In one embodiment, any excess centrate may be used to reduce the consistency of the wet cake so that it is suitable for the biological conversion and/or to provide an enzyme solution for the biological conversion.

In one embodiment, the centrate is periodically diverted from the cooling loop and relatively clean liquid is provided to replace the diverted centrate.

Advantageously, the flash tank 26 provides cooling of the biomass from the pretreatment temperature to a temperature compatible with microorganisms used in the biological conversion reactor 52 without using a vacuum flash tank and without diluting the biomass to a point that the hydraulic load of the decanter centrifuge 32 is exceeded. More specifically, the combination of using an atmospheric flash tank and cooling water cooled below about 50° C. provides maximum cooling with minimal water without the expense of using a vacuum flash.

Moreover, the use of the cooling system provides the means to cool the pretreated biomass without washing. More specifically, the system is more flexible with regards to whether the C5 sugars and/or other pretreatment sugars are removed and processed separately, or whether they remain with the solids.

Further advantageously, the flash tank 26 also allows the pretreated biomass to be mixed uniformly with a pH adjusting chemical. For example, in one embodiment wherein the biomass is held in the pretreatment reactor 16 under acidic conditions, a base or alkali 80 may be added to the centrate such that it is mixed with the pretreated biomass in the mixing zone of the flash tank 26.

In addition, the flash tank 26 provides the means to cool the pretreated biomass in a substantially closed-loop cooling system, which in one embodiment, does not affect the downstream biological conversion reaction(s) (e.g., does not substantially dilute the pretreated biomass slurry). Advantageously, this closed-loop cooling system provides relatively low water consumption and allows off the shelf components (e.g., pumps) to be used to transport the pretreated biomass. Accordingly, the process and/or system offer significant cost advantages compared to processes that use components for transporting medium consistency slurries. Furthermore, since the viscosity of the cooled slurry may be altered by controlling the temperature of the cooling liquid, the operator does not need to worry about the flow. Notably, the process control is achieved using relatively simple control loops.

Advantageously, the substantially closed-loop cooling system allows the pretreated biomass to be transported to a higher elevation using relatively inexpensive pumps with fewer complications. For example, since the centrate has a relatively low viscosity and/or is relatively free of undissolved solids, a standard centrifugal pump may be used to pump the cooled slurry to an inlet of the biological conversion reactor. Notably, this relatively high lift may not be possible with centrifugal pumps if the consistency is higher than about 15 wt %. Notably, since the centrate is likely to have a lower consistency than many process streams in the process (e.g., consider the cooling liquid used in US Pat. Pub. No. 2015/0240198), this desired slurry consistency may be achieved with less liquid.

Biological Conversion

The wet cake and/or excess centrate may be subject to a biological conversion 50 wherein microorganisms assist and/or accelerate the conversion of the biomass to a predetermined product (e.g., a transportation fuel such as ethanol, or another fuel or chemical product). In general, the biological conversion may include an enzymatic hydrolysis and/or fermentation.

The term "hydrolysis" refers to the production of sugars and/or short chain sugar oligomers from biomass. In general, hydrolysis may include the breaking of glycosidic bonds in polysaccharides to produce the sugars and/or sugar oligomers. For example, hydrolysis of cellulose may produce C6 sugars glucose, whereas hydrolysis of hemicellulose may produce C5 sugars such as xylose and arabinose in addition to some C6 sugars.

When a hydrolysis is assisted and/or accelerated with the use of an enzyme, the hydrolysis is referred to as an enzymatic hydrolysis. In one embodiment, cellulase enzymes are used to break cellulose chains into glucose. The term "cellulase" refers to any of several enzymes produced by fungi, bacteria, or protozoans that catalyze cellulolysis. For example, the term cellulase may denote a multi-enzyme mixture comprising exo-cellobiohydrolases (CBH), endo-glucanases (EG) and β-glucosidases ((βG) that can be produced by a number of plants and microorganisms.

The sugar(s) and/or sugar oligomers produced by the hydrolysis (e.g., the enzymatic hydrolysis and/or a chemical hydrolysis) may be fermented to an alcohol. For example, in one embodiment, the sugar(s) are fermented to ethanol. In another embodiment, the sugar(s) are fermented to methanol, butanol, or propanol. In another embodiment, the fermentation produces acetic acid, succinic acid, or another chemical.

In general, the fermentation may use yeast and/or bacteria. For example, in one embodiment, wherein the fermentation is part of an ethanol production, the fermentation is carried out with a *Saccharomyces* spp. yeast.

In one embodiment, glucose and/or other hexoses derived from the cellulose are fermented to ethanol using a wild-type *Saccharomyces cerevisiae* or a genetically modified yeast. In another embodiment, glucose is fermented to butanol using a microorganism such as *Clostridium acetobutylicum*.

Xylose and arabinose that are derived from the hemicelluloses may be fermented to ethanol using a yeast strain that naturally contains, or has been engineered to contain, the ability to ferment these sugars to ethanol. Examples of microbes that have been genetically modified to ferment xylose include recombinant *Saccharomyces* strains into which has been inserted either (a) the xylose reductase (XR) and xylitol dehydrogenase (XDH) genes from *Pichia stipitis* (see for example U.S. Pat. Nos. 5,789,210, 5,866,382, 6,582,944 and 7,527,927 and European Patent No. 450430) or (b) fungal or bacterial xylose isomerase (XI) gene (see for example U.S. Pat. Nos. 6,475,768 and 7,622,284). Examples of yeasts that have been genetically modified to ferment L-arabinose include, but are not limited to, recombinant *Saccharomyces* strains into which genes from either fungal (for example U.S. Pat. No. 7,527,951) or bacterial (for example WO 2008/041840) arabinose metabolic pathways have been inserted.

Alternatively, xylose and other pentose sugars may be fermented to xylitol by yeast strains selected from the group consisting of *Candida, Pichia, Pachysolen, Hansenula, Debaryomyces, Kluyveromyces* and *Saccharomyces*. Bacteria are also known to produce xylitol, including *Corynebacterium* sp., *Enterobacter liquefaciens* and *Mycobacterium smegmatis*.

In one embodiment, the hydrolysis and/or fermentation may be performed at or near the temperature and/or pH optimum of the corresponding microorganism. For example, conventional cellulase may have optimum pH values between about 4.5 and about 5.5 and a temperature optimum between about 40° C. and about 60° C., whereas *Saccharomyces cerevisiae* may have optimum pH values between about 4 and about 5.5 and a temperature optimum between about 25° C. and about 35° C. In one embodiment, the microorganism includes a yeast that naturally or genetically modified to have a temperature optimum above 58° C.

The dose of the microorganism will depend on other factors, such as the activity of the microorganism, the desired reaction time, the volume of the reactor and other parameters. It should be appreciated that these parameters may be adjusted as desired by one of skill in the art to achieve optimal conditions.

In one embodiment, the enzymatic hydrolysis and fermentation are conducted in separate vessels so that each biological reaction can occur at its respective optimal temperature. In another embodiment, the hydrolysis (e.g., which may be also referred to as saccharification) is conducted simultaneously with the fermentation in same vessel. For example, in one embodiment, a simultaneous saccharification and fermentation (SSF) is conducted at temperature between about 35 and 38° C., which is a compromise between the 50-55° C. optimum for cellulase and the 25-35° C. optimum for yeast.

Regardless of whether the biological conversion includes a separate hydrolysis and fermentation (SHF), simultaneous saccharification and fermentation (SSF), or hybrid hydrolysis and fermentation (HHF) (e.g., wherein the two separate steps are conducted in a same reactor, but at different temperatures), the reactor(s) may contain the C5 sugars and/or the C6 sugars. More specifically, the reactors may contain not only the glucose released during cellulose hydrolysis, but also one or more sugars arising from the pretreatment (e.g., xylose, glucose, arabinose, mannose, and/or galactose). For example, in one embodiment, excess centrate (e.g., which may have a relatively high concentration of C5 sugars) is fed to an enzymatic hydrolysis reactor with the solid component of the slurry, is fed to a fermentation reactor with C6 sugars provided by an enzymatic hydrolysis, and/or are processed in a separate fermentation reactor. For example, in one embodiment, separate fermentation reactors are provided for the C5 and C6 sugars, whereas in other embodiments, the C5 and C6 sugars are subject to co-fermentation in the same reactor or series of reactors.

In general, the hydrolysis and/or fermentation may be conducted in continuous, fed-batch, or batch mode. In one embodiment, the hydrolysis and/or fermentation are conducted in continuous mode, which may offer greater productivity and lower costs. For example, in one embodiment, the hydrolysis and/or fermentation tanks include one or more continuous stirred tank reactors (CSTRs) and/or one or more plug flow reactors (PFRs). In the plug flow reactor, the slurry is pumped through a pipe or tube such that it exhibits a relatively uniform velocity profile across the diameter of the pipe/tube and such that residence time within the reactor provides the desired conversion.

In one embodiment, the hydrolysis uses a plurality of hydrolysis reactors. For example, in one embodiment, the hydrolysis includes a plurality of hydrolysis rectors including a PFR and a CSTR in series, as for example, described in U.S. Pat. No. 8,709,770, which is hereby incorporated by reference.

In one embodiment, the hydrolysis is carried out in a hydrolysis system, which includes multiple hydrolysis reactors. The number of hydrolysis reactors in the system may depends on the cost of the reactors, the volume of the aqueous slurry, and/or other factors. For a commercial-scale ethanol plant, the typical number of hydrolysis reactors may be, for example, 4 to 12. In order to maintain the desired hydrolysis temperature, the hydrolysis reactors may be jacketed with steam, hot water, or other heat sources. The total residence time in the enzymatic hydrolysis reactors may be between about 24 hours and about 250 hours, depending on the degree of conversion desired.

Figure 5:
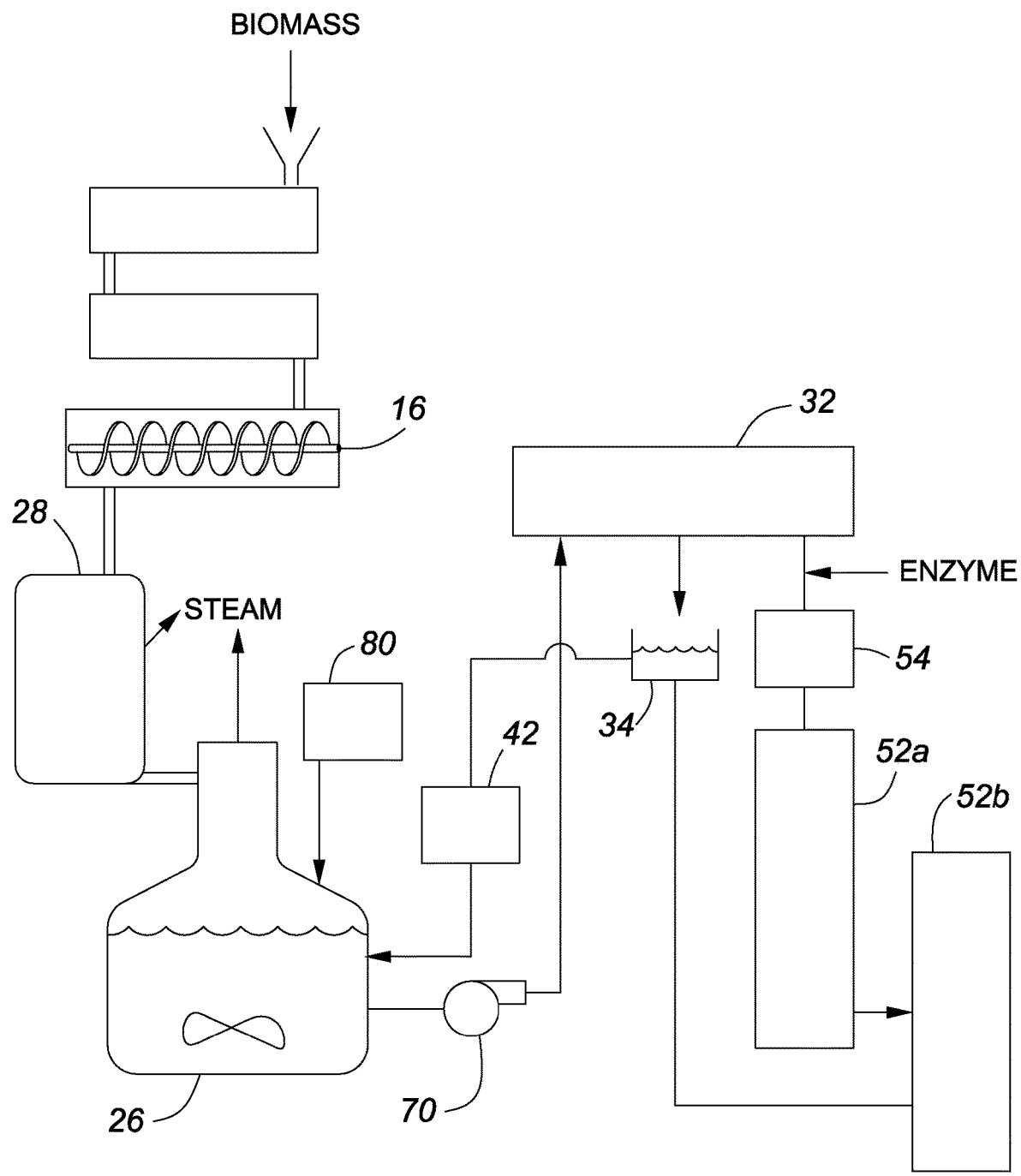
FIG. 5 is a schematic diagram showing a system for cooling pretreated biomass prior to hydrolysis in accordance with one embodiment of the instant invention.

Referring to FIG. 5, there is shown another embodiment of a cooling system for cooling and/or transporting the biomass to a plurality of hydrolysis reactors. In this embodiment, the pretreated biomass discharged from the pretreatment reactor 16 has a consistency that is lower than a consistency of the wet cake, such that excess centrate generated by the solids-liquid separating system 32 may be carried forward in the process. In this embodiment, hydrolysis is conducted in at least a first hydrolysis reactor 52a and a second hydrolysis reactor 52b, and the excess centrate is fed to an inlet of the second hydrolysis reactor, where it is eventually fed to one or more co-fermentation reactors. In other embodiments, the excess centrate is added back into the process at any stage prior to or during the co-fermentation. Introducing the excess centrate downstream from the first hydrolysis reactor advantageously allows the first hydrolysis reactor to operate under relatively high consistency conditions, thus providing longer retention times for the same vessel size (e.g., if the first reactor is a plug flow reactor). Accordingly, the instant embodiment is particularly advantageous if the first hydrolysis reactor 52a is a PFR and the second hydrolysis reactor is a CSTR. In this case, the excess centrate provides liquid that may facilitate hydrolysis and/or mixing in the CSTR.

In one embodiment, insoluble solids remaining after enzymatic hydrolysis, including lignin, are optionally removed using conventional solid-liquid separation techniques prior to any further processing. In another embodiment, the insoluble solids remaining after enzymatic hydrolysis are carried forward to fermentation.

In one embodiment, the fermentation uses a plurality of fermentation reactors. For example, in one embodiment, the hydrolysis uses a CSTR and/or a PFR.

In one embodiment, the fermentation reactors are agitated lightly with mechanical agitation. A typical, commercial-scale fermentation may be conducted using multiple reactors. In one embodiment, the fermentation microorganisms are recycled back to the fermentation prior to product recovery.

By the term "recovering", it is meant that the fermentation product is obtained in a more purified and/or concentrated form than that in the fermentation broth. The recovery may be carried out by any suitable technique known to those of ordinary skill in the art, and includes distillation for fermentation products that have a higher or lower boiling point than water, such as ethanol and butanol, or techniques such as liquid-liquid extraction for lactic acid.

If ethanol or butanol is the fermentation product, the recovery is carried out by distillation. Optionally, the fermentation product may be further concentrated by molecular sieves or membrane extraction.

EXAMPLES

Example 1

System for Cooling Pretreated Biomass Prior to Hydrolysis

The following describes a system for cooling pretreated biomass prior to hydrolysis in accordance with an embodiment of the invention.

Figure 6:
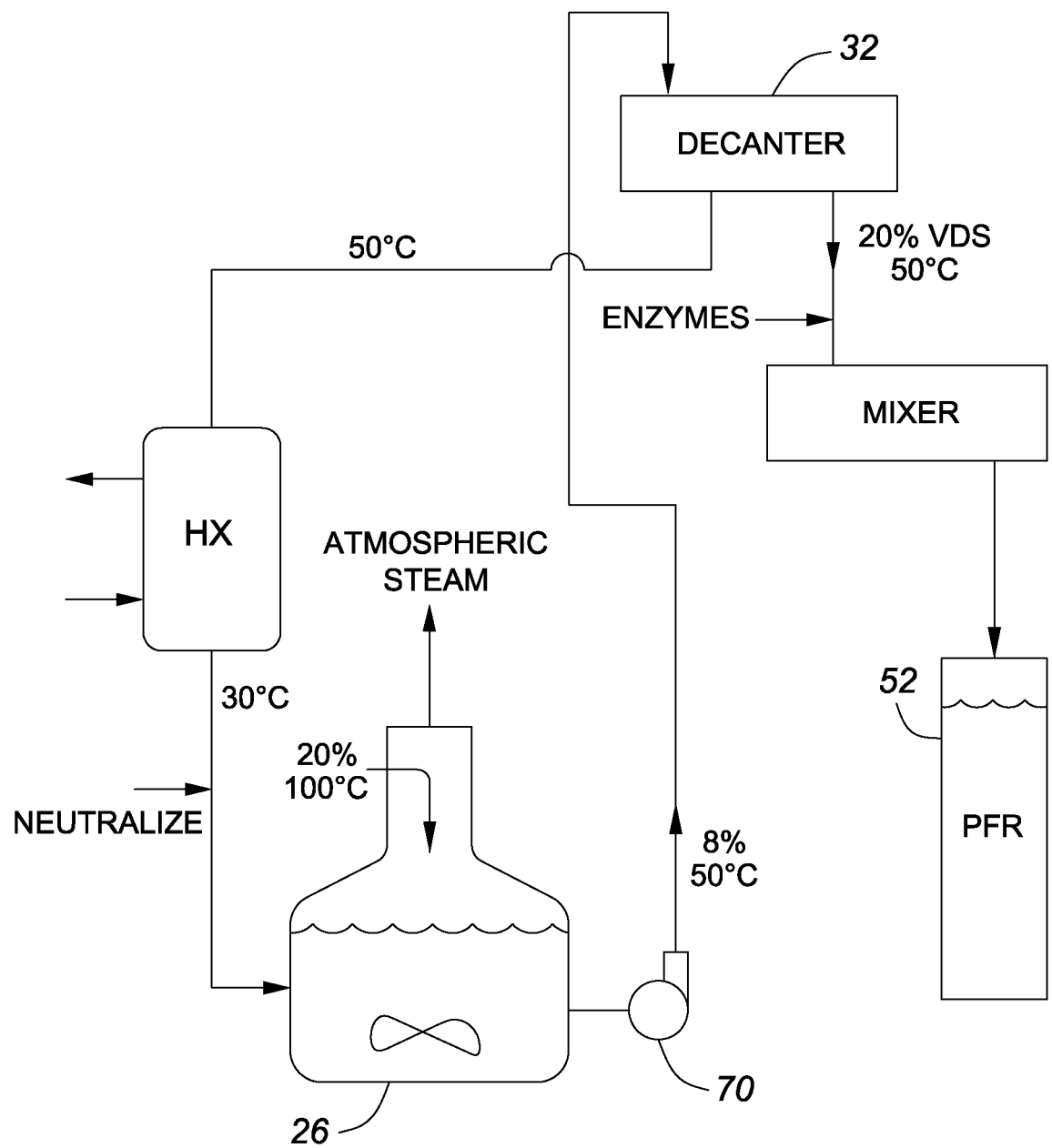
FIG. 6 is a schematic diagram showing an example of a system for cooling pretreated biomass prior to hydrolysis in accordance with one embodiment of the instant invention.

With reference to FIG. 6, pretreated biomass having a temperature of about 100° C. and a consistency of about 20 wt % is mixed with a cooling liquid in the flash tank 26. The cooling liquid, which has a temperature of about 30° C., is mixed with the pretreated biomass and exits the flash tank at an outlet near the mixing zone of the flash tank as a slurry having a having a temperature of about 50° C. and a consistency of about 8 wt %. The cooled slurry is pumped to a higher vertical elevation via a conventional centrifugal pump 70 and standard piping sized for the relatively low viscosity cooled slurry (e.g., having a consistency less than about 12 wt %). More specifically, the cooled slurry is pumped up to a decanter centrifuge 32, which separates the cooled slurry into a first stream comprising a liquid component of the slurry (e.g., the centrate) and a second other stream comprising a solid component of the slurry (e.g., the wet cake). The wet cake, which has a temperature of about 50° C. and a consistency of about 20 wt %, is fed to an inlet of plug flow reactor 52 after enzyme is mixed therein. The centrate, which has a temperature of about 50° C., is recycled back to the flash tank 26 after being cooled (e.g., by heat exchanger HX) to about 30° C.

Of course, the above embodiments have been provided as examples only. It will be appreciated by those of ordinary skill in the art that various modifications, alternate configurations, and/or equivalents will be employed without departing from the spirit and scope of the invention. For example, while the closed-loop cooling system is particularly advantageous when the inlet to the hydrolysis reactor is elevated relative to the outlet of the flash tank, it is also useful if the components and/or stages are at approximately the same elevation. Accordingly, the scope of the invention is therefore intended to be limited solely by the scope of the appended claims.

We claim:

1. A method for cooling and hydrolyzing pretreated biomass comprising:
    discharging pretreated biomass from a pretreatment reactor;
    mixing the discharged pretreated biomass with a cooling liquid in a vessel, the vessel including an outlet for providing a slurry;
    pumping the slurry to a solid-liquid separator, said solid-liquid separator for providing a first stream comprising a liquid component of the slurry and a second other stream comprising a solid component of the slurry;
    feeding at least a portion of the second other stream comprising the solid component to an inlet of a hydrolysis reactor;
    feeding at least a portion of the first stream comprising the liquid component to a cooling system to provide a cooled stream; and
    feeding at least a portion of the cooled stream to the vessel to provide cooling liquid,
    wherein the vessel is a flash vessel having a mechanical agitator, said flash vessel substantially at atmospheric pressure.

2. The method according to claim 1, comprising introducing a pH adjusting chemical to the discharged pretreated biomass, wherein introducing said pH adjusting chemical to the discharged pretreated biomass comprises adding the pH adjusting chemical to at least one of the at least a portion of the first stream fed to the cooling system, the at least a portion of the cooled stream, and a mixture comprising the discharged pretreated biomass and the cooling liquid.

3. The method according to claim 1, comprising introducing an enzyme to the second other stream comprising the solid component, wherein introducing the enzyme to the second other stream comprising the solid component comprises mixing the second other stream with enzyme in a mixer prior to feeding the second other stream to the inlet of the hydrolysis reactor.

4. The method according to claim 1, wherein the slurry has a consistency that is less than about 12 wt %, and wherein the second other stream comprising the solid component has a consistency greater than about 15 wt %.

5. The method according to claim 4, wherein the second other stream comprising the solid component has a consistency between about 18 wt % and 40 wt %.

6. The method according to claim 1, wherein the slurry has a consistency that is between about 5 wt % and about 12 wt %.

7. The method according to claim 1, wherein the slurry has a consistency that is less than about 15 wt %, and wherein a difference between the consistency of the slurry and the consistency of the second other stream comprising the solid component is at least 5 wt %.

8. The method according to claim 1, wherein the inlet to the hydrolysis reactor is elevated relative to the outlet of the vessel.

9. A method for cooling and hydrolyzing pretreated biomass comprising:
    discharging pretreated biomass from a pretreatment reactor;
    mixing the discharged pretreated biomass with a cooling liquid in a vessel, the vessel including an outlet for providing a slurry;
    pumping the slurry to a solid-liquid separator, said solid-liquid separator for providing a first stream comprising a liquid component of the slurry and a second other stream comprising a solid component of the slurry;
    feeding at least a portion of the second other stream comprising the solid component to an inlet of a hydrolysis reactor;
    feeding at least a portion of the first stream comprising the liquid component to a cooling system to provide a cooled stream; and
    feeding at least a portion of the cooled stream to the vessel to provide cooling liquid,
    wherein the pretreated biomass discharged from the pretreatment reactor has a consistency that is lower than a consistency of the second other stream comprising the solid component, and wherein a portion of the first stream comprising the liquid component is fed to a fermentation reactor.

10. A system for hydrolyzing biomass comprising:
    a pretreatment reactor for pretreating biomass prior to a hydrolysis reaction;
    a first cooling system in fluid communication with the pretreatment reactor for receiving pretreated biomass discharged from the pretreatment reactor, the first cooling system including a vessel having an inlet for receiving a cooling liquid, an agitator for mixing the pretreated biomass discharged from the pretreatment reactor with the cooling liquid, and an outlet for providing a slurry comprising pretreated biomass;
    a solid-liquid separating system for separating the slurry into a first stream comprising a liquid component of the slurry and a second other stream comprising a solid component of the slurry;
    a hydrolysis reactor in fluid communication with the solid-liquid separating system, the hydrolysis reactor having an inlet for receiving at least a portion of the second other stream comprising the solid component;
    a second cooling system for reducing the temperature of at least a first portion of the first stream comprising the liquid component to provide a cooled stream;
    at least one pipe for conveying at least a portion of the cooled stream to the vessel to provide cooling liquid; and
    a pump configured to transfer the slurry from the vessel to the solid-liquid separating system,
    wherein the vessel is an atmospheric flash tank having a mechanical agitator.

11. The system according to claim 10, wherein the first cooling system comprises a first flash tank upstream of the atmospheric flash tank.

12. A system for hydrolyzing biomass comprising:
    a pretreatment reactor for pretreating biomass prior to a hydrolysis reaction;
    a first cooling system in fluid communication with the pretreatment reactor for receiving pretreated biomass discharged from the pretreatment reactor, the first cooling system including a vessel having an inlet for receiving a cooling liquid, an agitator for mixing the pretreated biomass discharged from the pretreatment reactor with the cooling liquid, and an outlet for providing a slurry comprising pretreated biomass;

a solid-liquid separating system for separating the slurry into a first stream comprising a liquid component of the slurry and a second other stream comprising a solid component of the slurry;

a hydrolysis reactor in fluid communication with the solid-liquid separating system, the hydrolysis reactor having an inlet for receiving at least a portion of the second other stream comprising the solid component;

a second cooling system for reducing the temperature of at least a first portion of the first stream comprising the liquid component to provide a cooled stream;

at least one pipe for conveying at least a portion of the cooled stream to the vessel to provide cooling liquid; and a pump configured to transfer the slurry from the vessel to the solid-liquid separating system, wherein the first cooling system comprises an atmospheric flash tank disposed upstream of the vessel.

13. The system according to claim 10, wherein the second cooling system comprises a heat exchanger coupled to the at least one pipe.

14. The system according to claim 10, wherein the solid-liquid separating system comprises a decanter centrifuge.

15. The system according to claim 10, comprising a mixer disposed downstream of the solid-liquid separating system and upstream of the hydrolysis reactor for mixing enzyme with the at least a portion of the second other stream comprising the solid component.

16. The system according to claim 10, wherein said pretreatment reactor includes at least one inlet for injecting steam into the pretreatment reactor.

17. The system according to claim 10, wherein the pump comprises a centrifugal pump for conveying said slurry from the vessel up to the solid- liquid separating system.

18. The system according to claim 17, wherein said pump is a pump configured to transport slurries having a consistency that is less than about 12 wt %, and wherein said solid-liquid separating system comprises a solids-liquid separator configured for providing a solid component having a consistency between 15 wt % and 40 wt %.

19. A system for hydrolyzing biomass comprising:
a pretreatment reactor for pretreating biomass prior to a hydrolysis reaction;
a first cooling system in fluid communication with the pretreatment reactor for receiving pretreated biomass discharged from the pretreatment reactor, the first cooling system including a vessel having an inlet for receiving a cooling liquid, an agitator for mixing the pretreated biomass discharged from the pretreatment reactor with the cooling liquid, and an outlet for providing a slurry comprising pretreated biomass;

a solid-liquid separating system for separating the slurry into a first stream comprising a liquid component of the slurry and a second other stream comprising a solid component of the slurry;

a hydrolysis reactor in fluid communication with the solid-liquid separating system, the hydrolysis reactor having an inlet for receiving at least a portion of the second other stream comprising the solid component, wherein the hydrolysis reactor is a plug flow reactor:

a second cooling system for reducing the temperature of at least a first portion of the first stream comprising the liquid component to provide a cooled stream;

at least one pipe for conveying at least a portion of the cooled stream to the vessel to provide cooling liquid;

a pump configured to transfer the slurry from the vessel to the solid-liquid separating system; and a continuous stirred tank reactor having a first inlet in fluid communication with an outlet of the plug flow reactor and a second inlet for receiving a second other portion of the first stream comprising the liquid component.

20. A method for hydrolyzing biomass comprising:
reducing a pressure on pretreated biomass substantially to atmospheric pressure by discharging the biomass into a flash tank, the pressure reduction causing the biomass to cool from a first temperature to a second temperature;

mixing the discharged biomass with a cooling liquid in a mixing zone of the flash tank to form a slurry having a consistency that is less than about 12 wt %, the slurry at a third temperature, the third temperature lower than the second temperature;

pumping the slurry having a consistency that is less than about 12 wt % up to a solid -liquid separator, said solid-liquid separator for providing a first stream comprising a liquid component of the slurry and a second other stream comprising a solid component of the slurry, said second other stream having a consistency between about 15 wt % and about 40 wt %;

feeding at least a portion of the second other stream comprising the solid component to an inlet of a hydrolysis reactor;

feeding at least a portion of the first stream comprising the liquid component to a cooling system to provide a cooled stream, the cooled stream having a fourth temperature, the fourth temperature lower than the third temperature and less than about 50° C.; and feeding at least a portion of the cooled stream to the flash tank.

* * * * *